United States Patent
Oh et al.

(10) Patent No.: US 10,925,566 B2
(45) Date of Patent: *Feb. 23, 2021

(54) X-RAY IMAGING DEVICE AND X-RAY IMAGE FORMING METHOD

(71) Applicants: SAMSUNG ELECTRONICS CO., LTD., Suwon-si (KR); SAMSUNG LIFE PUBLIC WELFARE FOUNDATION, Seoul (KR)

(72) Inventors: Hyun Hwa Oh, Hwaseong-si (KR); Young Hun Sung, Hwaseong-si (KR); Kang Eui Lee, Seoul (KR); Myung Jin Chung, Seoul (KR)

(73) Assignees: SAMSUNG ELECTRONICS CO., LTD., Suwon-si (KR); SAMSUNG LIFE PUBLIC WELFARE FOUNDATION., Seoul (KR)

( * ) Notice: Subject to any disclaimer, the term of this patent is extended or adjusted under 35 U.S.C. 154(b) by 47 days.

This patent is subject to a terminal disclaimer.

(21) Appl. No.: 16/230,716

(22) Filed: Dec. 21, 2018

(65) Prior Publication Data

US 2019/0142355 A1 May 16, 2019

Related U.S. Application Data

(63) Continuation of application No. 15/293,788, filed on Oct. 14, 2016, now Pat. No. 10,201,319, which is a
(Continued)

(30) Foreign Application Priority Data

Sep. 5, 2012 (KR) .................... 10-2012-0098185

(51) Int. Cl.
*A61B 6/00* (2006.01)

(52) U.S. Cl.
CPC ............ *A61B 6/482* (2013.01); *A61B 6/4035* (2013.01); *A61B 6/463* (2013.01); *A61B 6/488* (2013.01);
(Continued)

(58) Field of Classification Search
CPC ....... A61B 6/482; A61B 6/4035; A61B 6/463; A61B 6/488; A61B 6/502; A61B 6/5217; A61B 6/545
(Continued)

(56) References Cited

U.S. PATENT DOCUMENTS 5,748,705 A  5/1998 Stein et al.
6,683,934 B1  1/2004 Zhao et al.
(Continued)

FOREIGN PATENT DOCUMENTS

CN  101422371 A  5/2009
CN  102335003 A  2/2012
(Continued)

OTHER PUBLICATIONS

Communication dated Nov. 26, 2019, from the European Patent Office in counterpart European Application No. 13183170.3.
(Continued)

*Primary Examiner* — Courtney D Thomas
(74) *Attorney, Agent, or Firm* — Sughrue Mion, PLLC

(57) ABSTRACT

An X-ray imaging apparatus includes an X-ray generator configured to generate X-rays and radiate the X-rays to an object; an X-ray detector configured to detect the X-rays that have passed through the object and convert the X-rays into a signal; and a controller configured to generate a single energy X-ray image and multiple energy X-ray images including a first X-ray image generated using an X-ray having determined energy band that is extracted from the X-rays detected by the X-ray detector. The multiple energy
(Continued)

X-ray images further include a second X-ray image in which a specific substance is separated, which is image is generated using the image signals corresponding to the energy bands from the detected X-rays, respectively, and the controller is further configured to control a display to display the single energy X-ray image and the first X-ray image and the second X-ray image on a screen of the display.

31 Claims, 16 Drawing Sheets

Related U.S. Application Data continuation of application No. 14/017,480, filed on Sep. 4, 2013, now Pat. No. 9,492,132.

(52) U.S. Cl.
CPC ............ *A61B 6/502* (2013.01); *A61B 6/5217* (2013.01); *A61B 6/545* (2013.01)

(58) Field of Classification Search
USPC .......................................................... 378/37
See application file for complete search history.

(56) References Cited

U.S. PATENT DOCUMENTS

| | | | |
|---|---|---|---|
| 6,898,263 | B2 | 5/2005 | Avinash et al. |
| 9,492,132 | B2 | 11/2016 | Oh et al. |
| 10,201,319 | B2 * | 2/2019 | Oh ....................... A61B 6/5217 |
| 2003/0215119 | A1 | 11/2003 | Uppaluri et al. |
| 2005/0195938 | A1 | 9/2005 | Zetterlund |
| 2007/0076842 | A1 | 4/2007 | Tkaczyk et al. |
| 2008/0232668 | A1 | 9/2008 | Kitamura et al. |
| 2009/0103679 | A1 | 4/2009 | Jabri et al. |
| 2009/0147919 | A1 | 6/2009 | Goto et al. |
| 2010/0061614 | A1 | 3/2010 | Hanke et al. |
| 2010/0131885 | A1 | 5/2010 | Licato et al. |
| 2010/0202675 | A1 * | 8/2010 | Takanaka ............... A61B 6/032 382/130 |
| 2011/0157154 | A1 | 6/2011 | Bernard et al. |
| 2011/0164797 | A1 | 7/2011 | Jang et al. |
| 2012/0014499 | A1 | 1/2012 | Feuerlein et al. |
| 2012/0051500 | A1 | 3/2012 | Johansson et al. |

FOREIGN PATENT DOCUMENTS

| | | |
|---|---|---|
| DE | 43 30 787 A1 | 3/1995 |
| DE | 10 2008 037 347 A1 | 2/2010 |
| DE | 10 2009 008 060 A1 | 8/2010 |
| DE | 10 2010 027 311 A1 | 1/2012 |
| EP | 0761166 A2 | 3/1997 |
| EP | 1216661 A2 | 6/2002 |
| EP | 2 428 163 A2 | 3/2012 |
| EP | 2705795 B1 | 8/2017 |
| JP | 9-262228 A | 10/1997 |
| JP | 2002330954 A | 11/2002 |
| JP | 2004-174232 A | 6/2004 |
| JP | 2004-174260 A | 6/2004 |
| JP | 2011-206240 A | 10/2011 |
| JP | 2014-50708 A | 3/2014 |
| JP | 5443237 B2 | 3/2014 |
| KR | 10-2004-0047561 A | 6/2004 |
| KR | 10-2010-0040652 A | 4/2010 |
| KR | 10-2011-0032047 A | 3/2011 |
| KR | 10-2012-0011679 A | 2/2012 |
| WO | 2012/080914 A1 | 6/2012 |

OTHER PUBLICATIONS

Communication dated Jul. 25, 2019 by the European Patent Office in counterpart European Patent Application No. 13183170.3.
Communication dated Sep. 24, 2019 by the Japanese Patent Office in counterpart Japanese Patent Application No. 2017-206417.
Communication dated Oct. 9, 2019 by the European Patent Office in counterpart European Patent Application No. 17185289.0.
Communication Part 1 dated May 28, 2018, issued by the European Patent Office in counterpart European application No. 13183170.3.
Communication Part 2 dated May 28, 2018, issued by the European Patent Office in counterpart European application No. 13183170.3.
Communication Part 3 dated May 28, 2018, issued by the European Patent Office in counterpart European application No. 13183170.3.
Communication Part 4 dated May 28, 2018, issued by the European Patent Office in counterpart European application No. 13183170.3.
Communication dated May 28, 2018, issued by the European Patent Office in counterpart European Application No. 13183170.3.
Communication dated Jul. 3, 2018, issued by the Japanese Patent Office in counterpart Japanese Patent Application No. 2017-206417.
Communication dated Sep. 26, 2017, from the Japanese Patent Office in counterpart application No. 2013-183059.
Communication dated Aug. 3, 2017, from the State Intellectual Property Office of People's Republic of China in counterpart Application No. 201310395362.0.
Communication dated Dec. 18, 2017, issued by the European Patent Office in counterpart European Patent Application No. 17185289.0.
Communication dated Feb. 4, 2017, issued by the State Intellectual Property Office of P.R. China in counterpart Chinese Application No. 201310395362.0.
Communication dated Nov. 25, 2013, issued by the European Patent Office in counterpart European Application No. 13183170.3.
Office Action dated Apr. 29, 2014, issued by the Korean Intellectual Property Office in counterpart Korean Application No. 10-2012-0098185.
Communication dated Apr. 25, 2017, from the Japanese Patent Office in counterpart application No. 2013-183059.
Communication dated Apr. 30, 2020 issued by the State Intellectual Property Office of P.R. China in counterpart Chinese Application No. 201710953370.0.
Communication dated Sep. 16, 2020 by the European Patent Office in counterpart European Patent Application No. 13183170.3.
Submission from Opponent dated Sep. 10, 2020 in counterpart European Patent Application No. 13183170.3.
Melnikow, Joy et al., "Supplemental Screening for Breast Cancer in Women With Dense Breasts: A Systematic Review for the U.S. Preventive Service Task Force", Evidence Synthesis, No. 126, ES14. 2016 (101 pages total).
Ciatto, Stefano et al., "A first evaluation of breast radiological density assessment by Quantra software as compared to visual classification", The Beast, Jan. 11, 2012, pp. 503-506, ES15. (5 pages total).
Anonymous, "Hologic's R2 Quantra Automates Breast Density Assessment Imaging Technology News", Technology, Sep. 30, 2008, https://www.itnonline.com/content/hologics-r2-quantra-automates-breast-density-assessment, ES16. (1 page total).

* cited by examiner

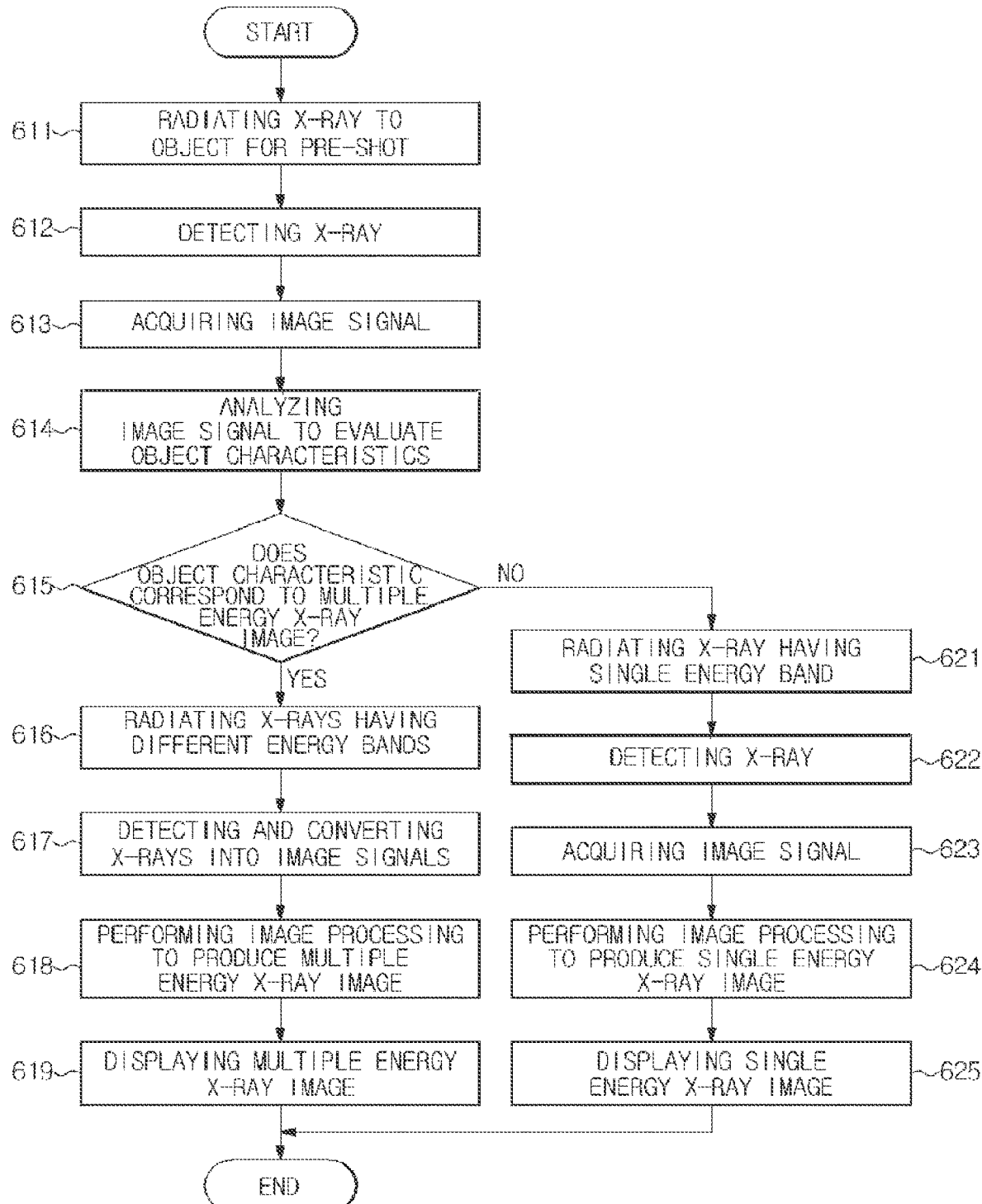

X-RAY IMAGING DEVICE AND X-RAY IMAGE FORMING METHOD

CROSS-REFERENCE TO RELATED APPLICATIONS

This is a continuation of U.S. application Ser. No. 15/293,788 filed Oct. 14, 2016, which is a continuation application of U.S. application Ser. No. 14/017,480 filed Sep. 4, 2013, which claims priority from Korean Patent Application No. 10-2012-0098185 filed on Sep. 5, 2012, in the Korean Intellectual Property Office. The disclosures of the above-identified applications are incorporated herein by reference in their entireties.

BACKGROUND

1. Field

Apparatuses and methods consistent with exemplary embodiments relate to generating an X-ray image which clearly distinguishes the internal tissues of the object.

2. Description of the Related Art

An X-ray imaging device generates images of an inner structure of an object by radiating X-rays to the object and analyzing X-rays passing through the object. X-ray transmittance varies depending on internal substances of the object, and an image of the inner structure of the object is acquired using an attenuation coefficient indicating transmittance as a numeric value.

In recent years, in order to increase a contrast between internal tissues of the object, a great deal of research has been conducted, and a method for acquiring X-ray images from a plurality of X-rays having different energy levels has been proposed.

SUMMARY

Exemplary embodiments may address at least the above problems and/or disadvantages and other disadvantages not described above. Also, the exemplary embodiments are not required to overcome the disadvantages described above, and an exemplary embodiment may not overcome any of the problems described above.

One or more of exemplary embodiments provide an X-ray imaging device to produce at least one of a single energy X-ray image and a multiple energy X-ray image depending on characteristics of an object, and a method for producing an X-ray image.

In accordance with an aspect of an exemplary embodiment, an X-ray imaging device includes an X-ray generator to generate X-rays and radiate the X-rays to an object, an X-ray detector to detect the X-ray passing through the object and acquire an image signal of the object, and a controller to evaluate a characteristic of the object based on the image signal and produce at least one of a single energy X-ray image and a multiple energy X-ray image according to the evaluated characteristic.

In accordance with an aspect of an exemplary embodiment, a method for producing an X-ray image includes: radiating an X-ray to an object; detecting the X-ray passing through the object and acquiring an image signal of the object, analyzing the image signal to evaluate a characteristic of the object, and producing at least one of a single energy X-ray image and a multiple energy X-ray image according to the evaluated characteristic.

BRIEF DESCRIPTION OF THE DRAWINGS

The above and/or other aspects will become more apparent by describing certain exemplary embodiments, with reference to the accompanying drawings, in which:

FIG. 11 is a flowchart illustrating a method for producing an X-ray image according to an exemplary embodiment;

DETAILED DESCRIPTION

Figure 1:
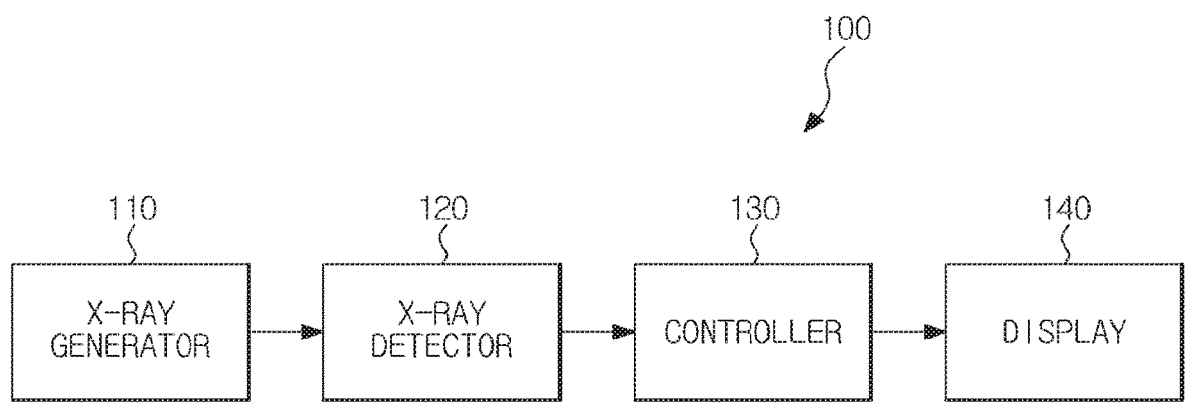
FIG. 1 is a block diagram illustrating a configuration of an X-ray imaging device according to an exemplary embodiment.

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

FIG. 1 is a block diagram illustrating a configuration of an X-ray imaging device.

Referring to FIG. 1, the X-ray imaging device or the X-ray imaging apparatus 100 includes an X-ray generator 110 to generate X-rays and radiate the same to an object, an X-ray detector 120 to detect X-rays passing through the object, a controller 130 to evaluate characteristics of the object using the detected X-rays and produce a single energy X-ray image or a multiple energy X-ray image, based on the evaluated results, and a display 140 to display the produced X-ray image.

The X-ray generator 110 generates X-rays having a predetermined energy level and radiates the same to the object. The X-ray generator 110 receives power from a power supply (not shown) and generates X-rays. The X-ray energy may be controlled by a supplied tube voltage and the X-ray intensity or dose may be controlled by a tube current and an X-ray exposure time.

Although X-rays radiated from the X-ray generator 110 may be monochromatic X-rays or polychromatic X-rays, a configuration in which polychromatic X-rays are radiated from the X-ray generator is described below with reference to exemplary embodiments, for convenience of description.

The X-ray generator 110 radiates X-rays having a predetermined energy band, and an energy band of the radiated X-rays is defined by an upper limit and a lower limit. X-ray energy may be represented as average energy, maximum energy, energy band or the like. In an exemplary embodiment, X-ray energy is represented by an X-ray energy band or maximum energy of the X-ray energy band.

The upper limit of the energy band, that is, the maximum energy of radiated X-ray is controlled by a level of tube voltage, and energy band lower limit, that is, a minimum energy of radiated X-rays is controlled by a filter provided inside or outside the X-ray generator 110. When X-rays with a low energy band are filtered through the filter, radiated average X-ray energy is increased.

The X-ray detector 120 detects X-rays passing through the object and converts the detected X-rays into electrical signals. X-rays radiated from the X-ray generator 110 pass through the object and are attenuated. An attenuation ratio of X-rays varies depending on characteristics of tissues of an object area, to which the X-rays are radiated, or thickness of the object area, and an amount of detected X-rays varies depending on the inner composition of the object. The object is imaged by using the electrical signal of the X-ray detector 120 and a signal output from the X-ray detector 120 is a type of image signal.

The X-ray detector 120 acquires a plurality of image signals with different energy bands. According to an exemplary embodiment, a method of acquiring image signals includes a method including radiating respectively a plurality of X-rays having different energy bands by the X-ray generator 110 and detecting respectively the plurality of X-rays by the X-ray detector 120, and a method including radiating X-rays having a predetermined energy band by the X-ray generator 110 and dividing the X-rays into specific energy bands by the X-ray detector 120. The different energy bands may have at least one of upper and lower limits of energy bands which are different from one another.

The controller 130 analyzes the image signal acquired by the X-ray detector 120 and evaluates characteristics of the object. The characteristics of the object include at least one of structures of the tissues constituting the object, ratios of respective tissues and densities of specific tissues, and another characteristic of the object evaluated by the controller 130 may be used as a characteristic of the object so long as it determines an X-ray image which is easy to analyze.

The controller 130 generates at least one of a single energy X-ray image and a multiple energy X-ray image, based on the evaluation results of the object. The single energy X-ray image means an X-ray image which is produced by detecting X-rays having a single energy band, and the multiple energy X-ray image means an X-ray image which is produced by detecting a plurality of X-rays having different energy bands and increasing a contrast between components of the object using the X-rays detected.

An image signal produced from X-rays having a single energy band exhibits good signal-to-noise ratio (SNR) and a single energy X-ray image thus exhibits superior spatial resolution and contrast. The multiple energy X-ray image has a high contrast between tissues and is thus useful for specific tissues such as lesions.

Accordingly, when an image with a high contrast between tissues is needed depending on characteristics of the object, a multiple energy X-ray image is produced, and when an image with low contrast between tissues is not needed, a single energy X-ray image with good signal-to-noise ratio is produced.

In an exemplary embodiment, the controller 130 produces a multiple energy X-ray image with increased contrast between tissues, when the object has a dense tissue having a high ratio of fat tissue to parenchymal tissue, and the controller 130 produces a single energy X-ray image, when the object has a tissue having a high ratio of parenchymal tissue to fat tissue.

The controller 130 analyzes an image signal acquired by pre-shot and controls imaging conditions such as tube voltage and tube current supplied to the X-ray generator 110 and X-ray exposure time. The pre-shot aims at controlling X-ray imaging conditions depending on characteristics of the object prior to main imaging and is performed at X-rays dose decreased by controlling tube current and X-ray exposure time. Also, the controller 130 may select a target material (anode) used for X-ray generation in the X-ray generator 110, or a filter used for filtering the generated X-ray.

The display 140 displays the X-ray image generated by the controller 130 for a user to perform diagnosis by analyzing the image.

In a case in which the object is human body, the X-ray imaging device may be used to image the chest, mouth, breasts and various other tissues, organs, or bones of the human body according to an application and the structure of the X-ray imaging device may be slightly changed according to imaging area.

Although the X-ray imaging device has no restrictions as to imaging area, for convenience of description, a detailed operation of the mammography X-ray imaging device is described below with reference to an exemplary embodiment.

Figure 2:
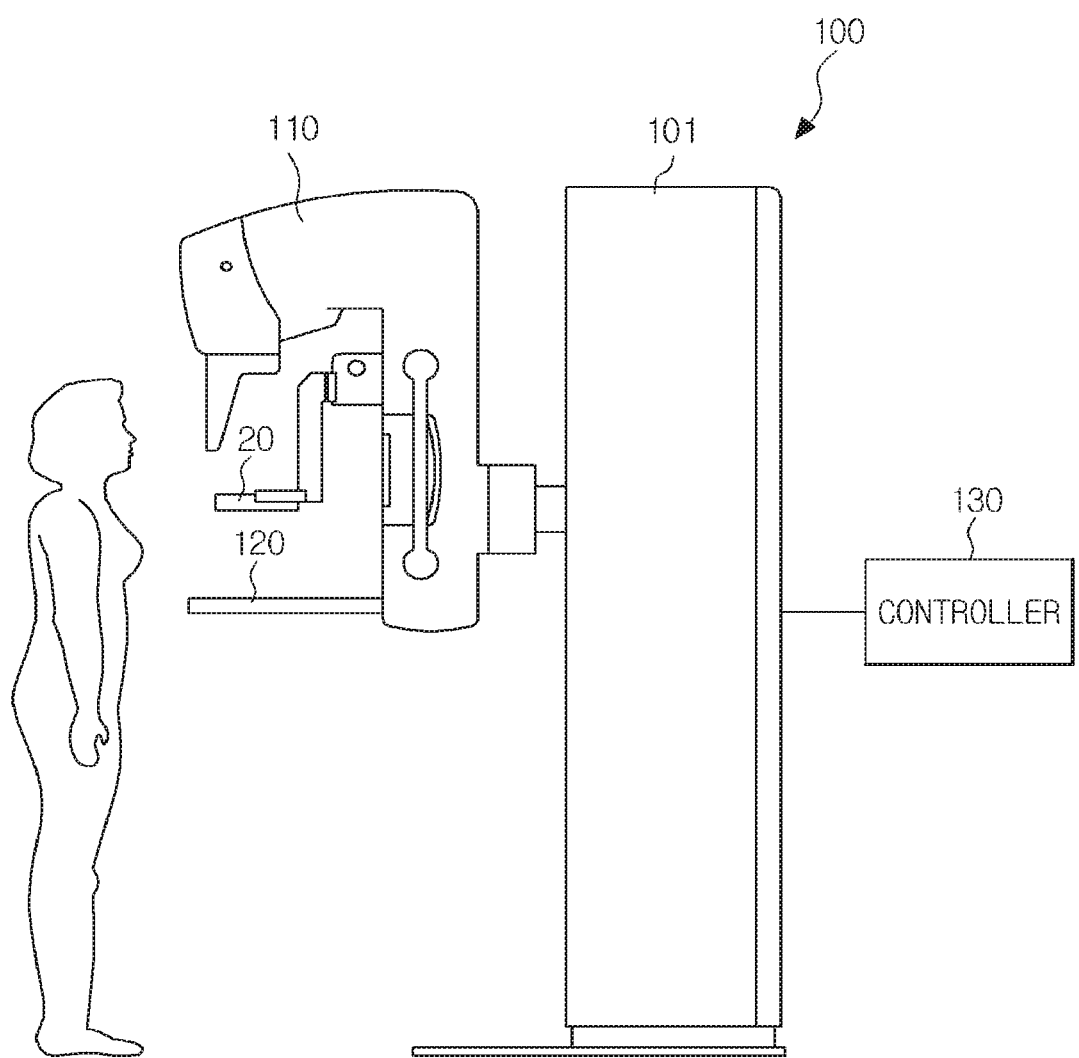
FIG. 2 illustrates an overall appearance of an X-ray imaging device to image breasts according to an exemplary embodiment.
Figure 3:
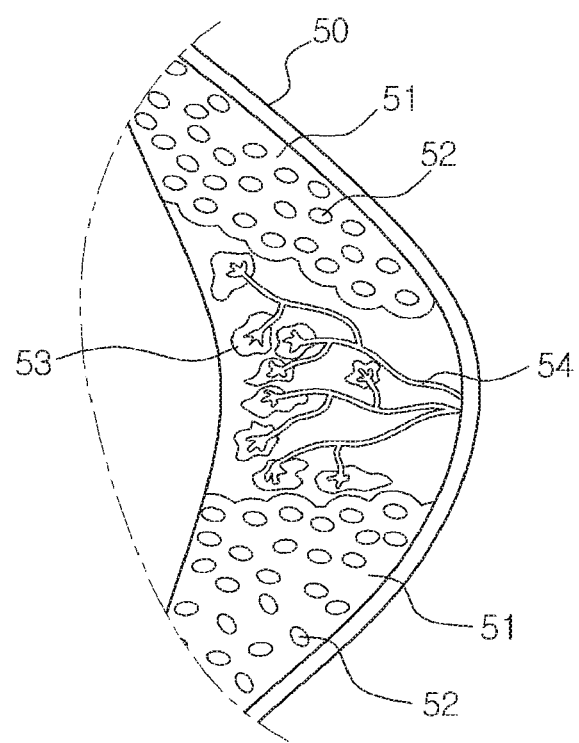
FIG. 3 is a sectional view illustrating a tissue composition of a breast.

FIG. 2 illustrates an overall exterior appearance of an X-ray imaging device to image breast according to an exemplary embodiment. FIG. 3 is a sectional view illustrating an internal composition of a breast.

Referring to FIG. 2, the X-ray imaging device 100 to image breasts includes a housing 101 to support the X-ray generator 110 and the X-ray detector 120, and a compression paddle 20 to compress the breast. A breast is disposed between the X-ray detector 120 and the compression paddle 20, to reduce a thickness of the breast by compression using the compression paddle 20, and X-rays are irradiated using the X-ray generator 110, to perform X-ray imaging.

The controller 130 controls X-ray imaging conditions depending on breast characteristics and for this purpose, the X-ray imaging device performs pre-shot to evaluate characteristics of the breast.

The controller 130 analyzes an image signal acquired by pre-shot, estimates or calculates a density of breast and a thickness of compressed breast and determines imaging conditions suitable for characteristics of the object using these properties as analysis factors. Information associated with the thickness of the compressed breast may be acquired from the compression paddle 20.

The controller 130 may be provided in a workstation or a host device to control an operation of the X-ray imaging device, but a position thereof is not limited.

Referring to FIG. 3, the tissues of the breast 50 include fibrous tissue 51 which surrounds the breast periphery and supports the breast shape, fat tissue 52 distributed throughout the breast, a breast gland tissue 53 to produce human milk, and a breast duct tissue 54 to provide a passage for breast milk and the like. Tissues associated with production and supply of breast milk, such as the breast gland tissue 53 and the breast duct tissue 54, are referred to as parenchymal tissues of breast. The parenchymal tissues have similar lesions, such as tumors, and similar X-ray absorbance. Accordingly, it is difficult to detect lesions from a breast X-ray image in which parenchymal tissues are dense and/or large, and it is relatively easy to detect lesions in a breast X-ray image in which little parenchymal tissue is present.

Accordingly, when the breast 50 is a dense breast in which parenchymal tissues are dense, a multiple energy X-ray image with an increased contrast between tissues is produced. When the breast 50 has less density, a single energy X-ray image with a superior signal-to-noise ratio is produced.

As described above, the method for producing a multiple energy X-ray image is divided into irradiation of a plurality of X-rays with different energy bands from the X-ray generator 110 and separation of X-rays detected from the X-ray detector 120 according to respective energy bands.

Figure 4:
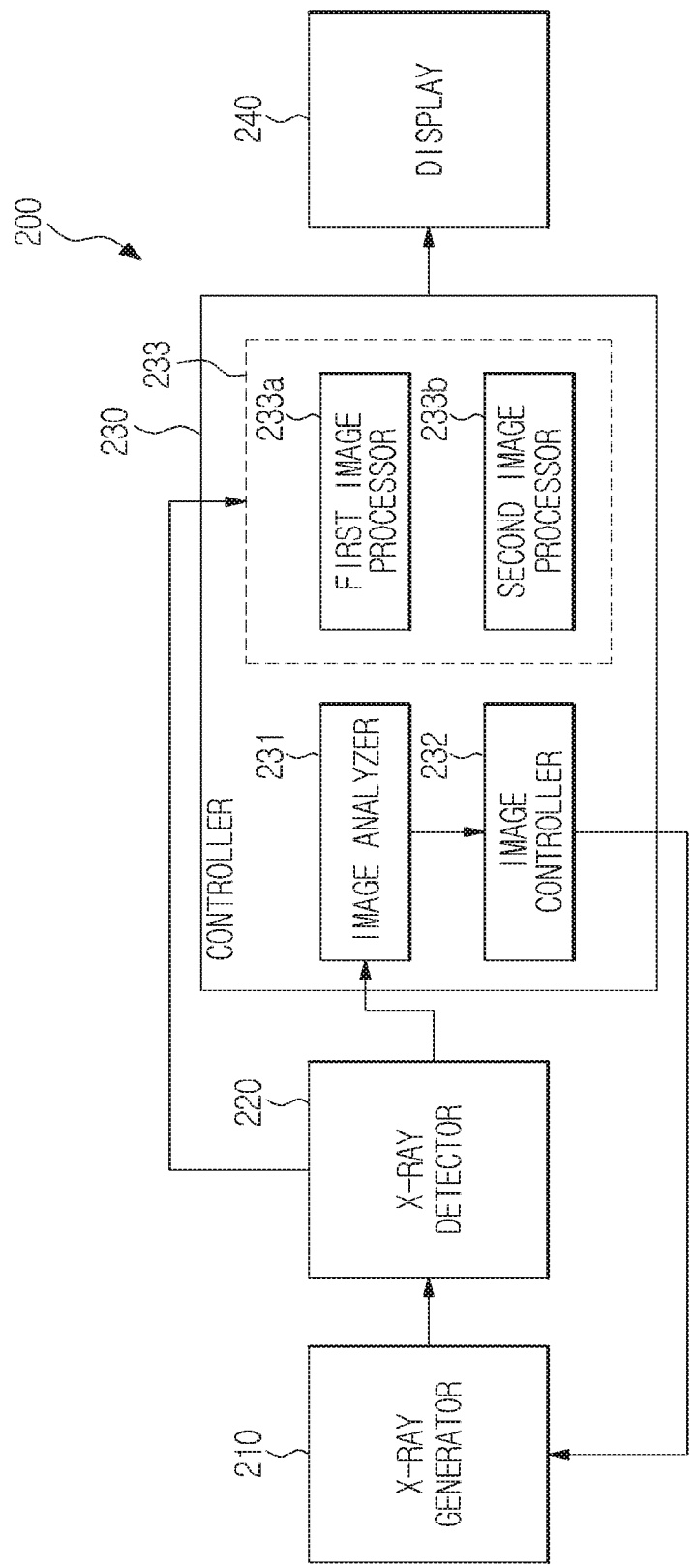
FIG. 4 is a block diagram illustrating an X-ray imaging device according to an exemplary embodiment in detail.

FIG. 4 is a block diagram illustrating X-rays imaging device according to an exemplary embodiment in detail.

The X-ray imaging device 200 according to the present exemplary embodiment radiates X-rays with different energy bands to produce a multiple energy X-ray image and performs pre-shot prior to main imaging.

Basic operations of the X-ray generator 210, the X-ray detector 220 and the display 240 have been described above with reference to FIG. 1.

The controller 230 includes an image analyzer 231 to analyze the image signal acquired by the X-ray detector 220 and evaluate characteristics of the object, an image controller 232 to determine X-ray imaging conditions depending on characteristics of the object, and an image processor 233 to produce a single energy X-ray image or a multiple energy X-ray image using the image signal acquired by the X-ray detector 220.

First, the X-ray generator 210 radiates X-rays having a lower dose, as compared to the main imaging, to perform pre-shot. The X-ray detector 220 detects X-rays passing through the object during pre-shot and acquires an image signal of the object. In an exemplary embodiment, pre-shot may be performed by adjusting X-ray dose to about 4 mAs.

The image analyzer 231 analyzes the image signal acquired by the X-ray detector 220 and evaluates characteristics of the object.

For example, the image analyzer 220 determines the breast density. As described above with reference to FIG. 3, when parenchymal tissues of breast are dense and/or large, it is not easy to detect lesions in the breast tissue. A growth or a size degree of parenchymal tissues in the breast is referred to as breast density.

In an exemplary embodiment in which the image analyzer 231 determines breast density, a breast region is extracted from the image signal acquired by the X-ray detector 220 and a region to be estimated as a parenchymal tissue is extracted from the breast region. A ratio of an area of the parenchymal tissue region with respect to a total area of the breast region is calculated to represent the breast density.

Specifically, the region corresponding to the parenchymal tissue is estimated as a region which has a high image signal brightness or intensity. For example, a predetermined first value is compared with the brightness or intensity of the image signal in each pixel region of the breast. When the brightness or intensity of the image signal exceeds the first value, the corresponding pixel region is estimated to belong to the parenchymal tissue. The first value may be predetermined through experimentation, statistics or theoretically.

The image controller 232 controls main imaging based on characteristics of the object evaluated by the image analyzer 231. Specifically, the image controller 232 determines whether a single energy X-ray image or a multiple energy X-ray image is to be acquired by main imaging, based on characteristics of the object and controls the X-ray generator 210 based on the results. That is, when the characteristic of object corresponds to a single energy X-ray image, the single energy X-ray image is acquired, and when the characteristic of object corresponds to a multiple energy X-ray image, the multiple energy X-ray image is acquired.

When the breast density calculated by the image analyzer 231 exceeds a predetermined second value, the characteristic of object is determined to correspond to the multiple energy X-ray image, and when the breast density calculated by the image analyzer 231 does not exceed the predetermined second value, the characteristic of object is determined to correspond to the single energy X-ray image. The second standard value means a standard value which determines that the breast as the object is a dense breast.

The second value may be predetermined by a designer or a user. For example, when a breast density exceeds 50%, the breast is determined to be a dense breast in accordance with the classification standard of breast imaging reporting and database system (BI-RADS). However, an exemplary embodiment of the X-ray imaging device 200 is not limited thereto and other standard values may be set through experimentation or theoretically.

The image controller 232 may control imaging conditions such as tube voltage and tube current supplied to the X-ray generator 210 and X-ray exposure time depending on object characteristics.

When the characteristic of object corresponds to a multiple energy X-ray image, the X-ray generator 210 respectively radiates a plurality of X-rays having different energy bands for main imaging. The energy bands of radiated X-rays may be set according to type or characteristics of object.

Figure 5:
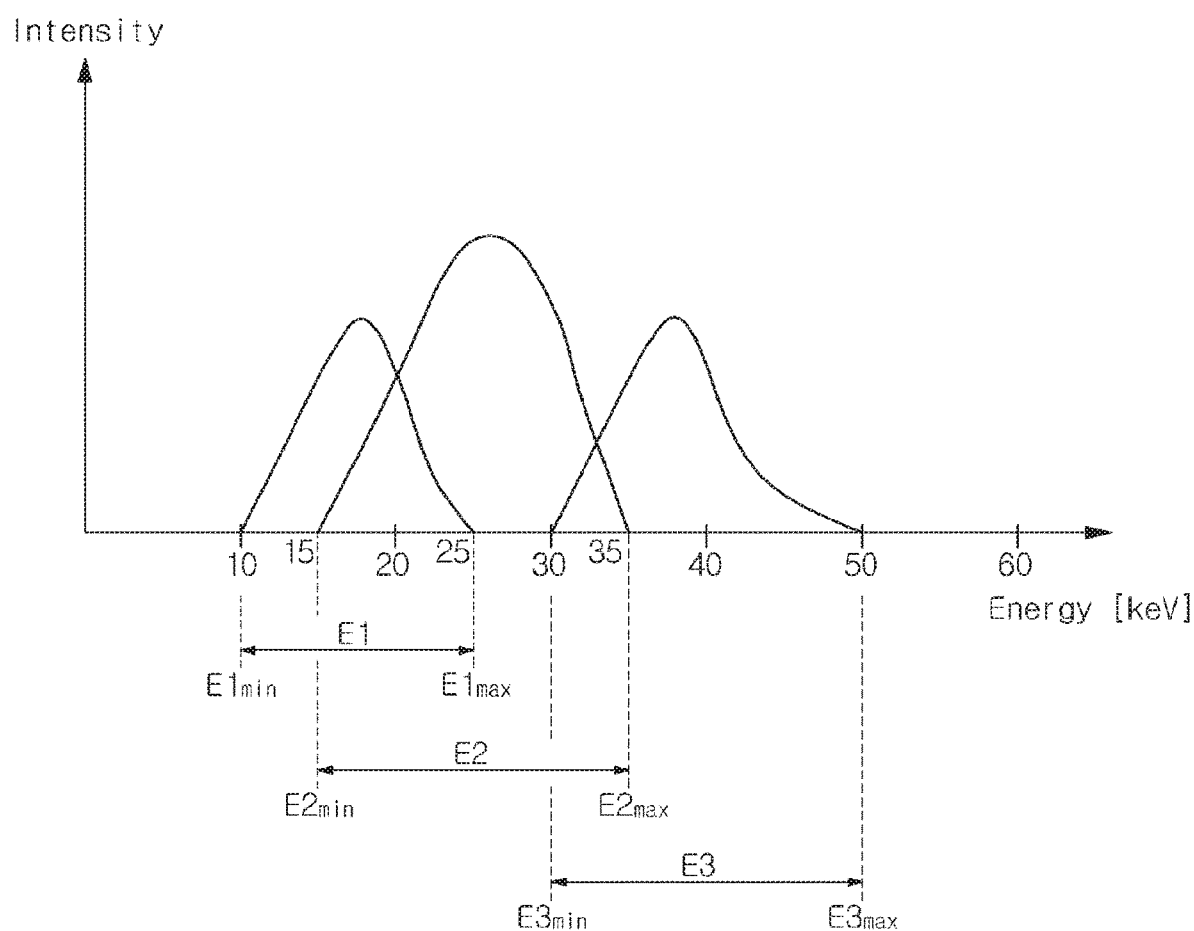
FIG. 5 is a graph showing energy bands of an X-ray radiated from the X-ray imaging device.

FIG. 5 is a graph showing energy bands of X-rays radiated from the X-ray imaging device.

Referring to FIG. 5, the X-ray generator radiates X-rays with a first energy band E1, X-rays with a second energy band E2 and X-rays with a third energy band E3 and the energy bands may partially overlap one another.

In an exemplary embodiment in which X-rays with different energy bands are radiated, in order to radiate the X-ray with a first energy band E1, a tube voltage of about 25 kVp is supplied to the X-ray generator 210 to generate X-rays with a maximum energy $E1_{max}$ of about 25 keV. The X-ray generator 210 adjusts a minimum energy $E1_{min}$ of the radiated X-rays to about 10 keV using the filter provided inside or outside the device. As a result, X-rays having the first energy band E1 (about 10 to about 25 keV) are emitted.

Similarly, in order to radiate X-rays with a second energy band E2, a tube voltage of about 35 kVp is supplied to the X-ray generator 210 to generate X-rays having a maximum energy $E2_{max}$ of about 35 keV. The X-ray generator 210 adjusts a minimum energy $E2_{min}$ of emitted X-rays to about 15 keV using the filter. As a result, X-rays having the second energy band E2 (about 15 to about 35 keV) are emitted.

Similarly, in order to radiate X-rays with a third energy band E3, a tube voltage of 50 kVp is supplied to the X-ray generator 210 to generate X-rays having a maximum energy $E3_{max}$ of about 50 keV. The X-ray generator 210 adjusts a minimum energy $E3_{min}$ of emitted X-rays to about 30 keV using the filter. As a result, X-rays having the third energy band E3 (about 30 to about 50 keV) are emitted.

Referring to FIG. 4 again, the X-ray detector 220 detects a plurality of X-rays passing through the object, acquires a plurality of image signals of respective energy bands from the detected X-rays and transmits the image signals to a first image processor 233a. The first image processor 233a performs multiple energy image processing on the transmitted image signals to produce a multiple energy X-ray image with an increased contrast between tissues.

The multiple energy image processing is an image processing method for producing an image having an increased contrast between soft tissues and lesions having similar X-ray absorbance from a plurality of image signals having different energy bands, or an image having an increased contrast of soft tissues and hard tissues (such as bones or calcified materials) and any multiple energy image processing may be used in the X-ray imaging device.

Hereinafter, a multiple energy image processing method will be described in more detail.

Figure 6:
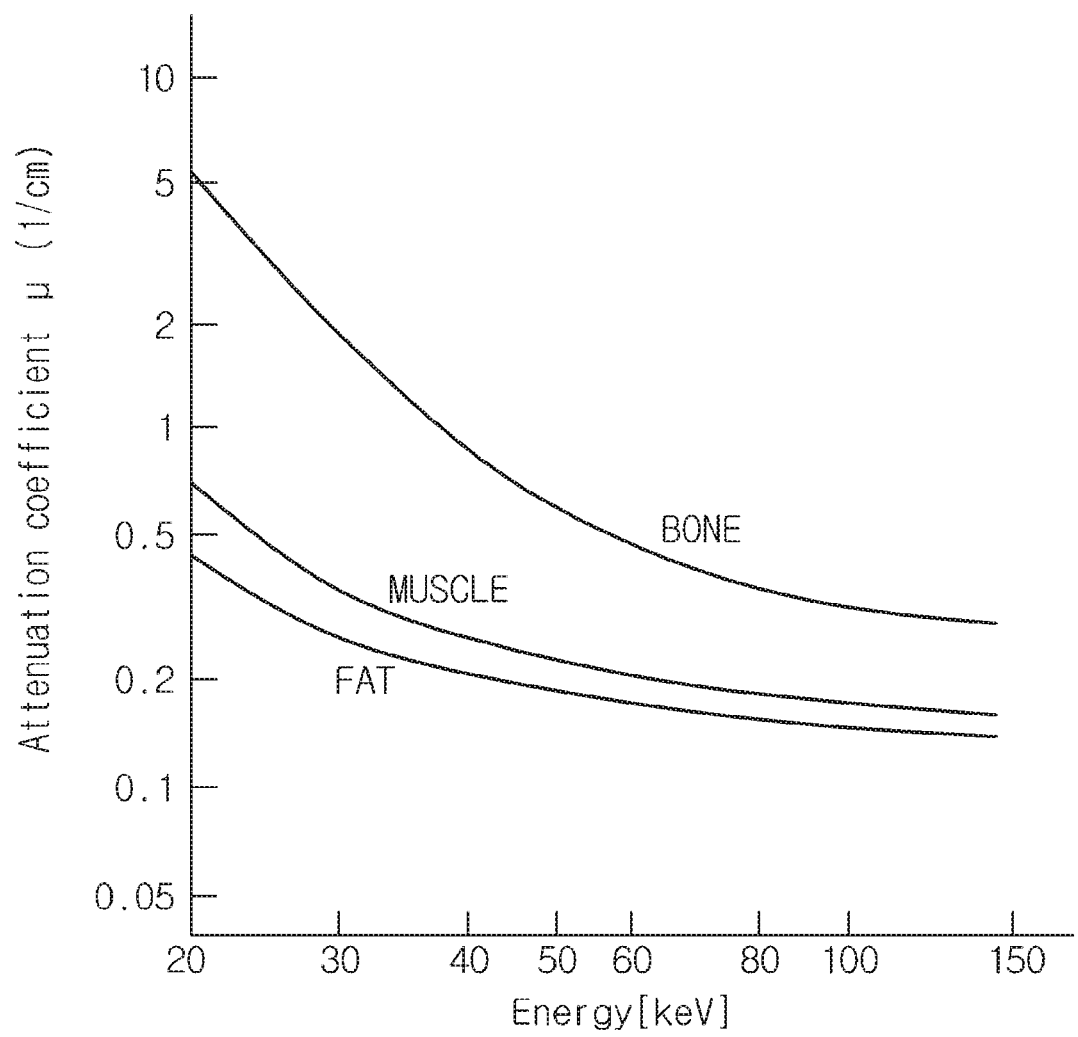
FIG. 6 is a graph schematically showing variation in attenuation coefficient of X-rays, with respect to individual substances constituting the human body.

FIG. 6 is a graph schematically showing variation in attenuation coefficient with respect to individual substances constituting the human body.

As described above, X-ray transmittance is changed depending on characteristics of an object, through which the X-ray passes, and this is defined as an attenuation coefficient.

FIG. 6 shows variation in attenuation coefficient as a function of X-ray energy with respect to bone, muscle and fat of the human body. As shown in FIG. 6, bone, muscle and fat exhibit different variations in attenuation coefficient and the difference in attenuation coefficient between substances is changed according to X-ray energy.

Although variations in attenuation coefficient of bone, muscle, and fat are illustrated in FIG. 6, the attenuation coefficient varies between various soft tissues containing fat. Accordingly, by using a plurality of image signals with different energy bands, substances having different attenuation properties may be extracted from one image.

Assuming that an attenuation coefficient of X-rays of $N_0$ photons having an energy E is $\mu(E)$, the number N of photons after passing through an object having a thickness T is represented by the following Equation 1.

$$N = N_0 * e^{-\mu(E)T}$$ [Equation 1]

Assuming that a thickness of the $m^{th}$ substance is $T_m$ and the number of types of substances, through which X-rays pass, is M, the Equation 1 may be represented by the following Equation 2.

$$N = N_0 * e^{-\{\mu 1(E)T1 + \mu 2(E)T2 + \ldots + \mu M(E)TM\}}$$ [Equation 2]

Based on Equation 2, an image pixel value is determined by dividing both sides by a measurable value $N_0$ and applying antilogarithm (−log). In the same manner, when a number L of X-ray images are acquired from the number L of different energies $E_1, E_2, \ldots, E_L$, the pixel value $I(E_1)$ may be represented by the following Equation 3.

$$I(E_1) = -\log(N(E_1)/N_0) = \mu_1(E_1)T_1 + \mu_2(E_1)T_2 + \ldots + \mu_M(E_1)T_M$$ [Equation 3]

Accordingly, L equations associated with respective pixels according to the Equation 3 are acquired from the number L of X-ray images and this is represented by a matrix formula in the following Equation 4.

$$I = \mu \cdot T$$ [Equation 4]

Accordingly, if L=M, images of respective substances are acquired by calculating a matrix operation of $T = \mu^{-1} \cdot I$. Equation 4 is derived based on an ideal monochromatic X-ray image, but a modification of Equation 4 may be used when X-rays having a predetermined energy band image are used.

The multiple energy X-ray image produced by the first image processor 233a may be a plurality of images separated according to respective substances, an image of only a specific substance, a region in which a ratio difference between substances is out of a normal range is diacritically marked as an abnormal tissue using the images separated according to respective substances, or an image in which the plurality of images are combined and the respective substances are diacritically marked in one image.

As a multiple energy image processing method according to another embodiment, there is a method for acquiring image signals with non-imaged other energy bands from image signals with different energy bands.

As shown in FIG. 6, generally, a difference in attenuation coefficient between the substances decreases, as X-ray energy increases, and increases, as X-ray energy decreases. Accordingly, X-rays with a low energy band in which a difference in attenuation coefficient between the substances is great may be used to obtain a breast X-ray image consisting of soft tissues such as parenchymal tissue, fat tissue and fibrous tissue.

However, since use of X-ray with a low energy band is restricted due to limitations as to physical properties or X-ray dose, an X-ray image with increased contrast between substances is produced by obtaining image signals regarding energy bands which may be imaged without great limitation of X-ray dose and estimating an image signal regarding a low energy band showing a great difference in attenuation coefficient between the substances from these image signals.

The above-described exemplary embodiments are examples of generating a multiple energy X-ray image, but this is not limiting.

The produced image is displayed on the display 240 and a user easily detects lesions on an image with an increased contrast ratio.

Referring to FIG. 4 again, the image controller 232 controls the X-ray generator 210 to radiate X-rays having a single energy band to an object, when the characteristic of object corresponds to a single energy X-ray image, that is, the breast is determined not to be a dense breast.

The X-ray detector 220 detects X-rays passing through the object and acquires an image signal of the object. The acquired image signal is transmitted to the second image processor 233b which subjects the image signal to image processing to produce an X-ray image. The image processing may include noise removal, edge enhancement or contrast ratio adjustment to produce a single energy X-ray image.

Specifically, the second image processor 233b controls gradation and frequency properties of images by gradation processing and frequency processing, improves image quality through spatial frequency processing and realizes objective image enhancement by gradation processing. Details of such image processing are known to those skilled in the art and a detailed explanation thereof will be omitted.

The produced X-ray image is displayed on the display 240 and a user analyzes the X-ray image with a superior signal-to-noise ratio (SNR) and thereby detects lesions.

In the above-described exemplary embodiment, the image signal acquired during pre-shot is analyzed and characteristics of the object are evaluated. However, in an exemplary embodiment an image of main imaging may be analyzed and characteristics of the object may be evaluated instead of or in addition to the pre-shot.

Specifically, the X-ray generator 210 radiates X-rays with a first energy band to an object and the X-ray detector 220 detects X-rays passing through the object to acquire an image signal. The first energy band corresponds to an energy band to produce a single energy X-ray image and is set by pre-shot or according to object type (chest, abdomen, breast and other skeletons) without pre-shot. For example, when chest is used as the imaging region, a high energy band having a maximum energy of about 140 keV is set at a first energy band and, when a breast is used as the imaging region, a low energy band having a maximum energy of about 30 keV is set at the first energy band.

The acquired image signal is transmitted to the image analyzer 231 and the image analyzer 231 analyzes the image signal and evaluates characteristics of the object. A method for evaluating characteristics of the object is described above.

When the characteristic of object evaluated by the image analyzer 231 corresponds to a multiple energy X-ray, the image controller 232 controls the X-ray generator 210 to radiate X-rays with a second energy band to an nth energy (n≥2, n is an integer) band, the X-ray detector 220 detects the X-rays and converts the x-rays into image signals. Here, n may be set depending on characteristics of the object and an order of n is not related to an energy level.

For example, when imaging the chest, n is set at 2 and X-rays with an energy band having a maximum energy of about 70 keV are radiated, and when imaging the breast, n is set at 2 and X-rays with an energy band having a maximum energy of about 50 keV are radiated. High energy and low energy are relative concepts. That is, when chest is imaged, X-rays with an energy band having a maximum energy of about 70 keV are X-rays with a low energy band, and when breast is imaged, an X-ray with an energy band having a maximum energy of about 50 keV is an X-ray with a high energy band.

The converted image signal is transmitted to the first image processor 233a which performs multiple energy image processing on an image signal corresponding to the first energy band and an image signal corresponding to the remaining energy band, produces a multiple energy X-ray image with increased contrast between tissues and displays the image on the display 240.

When the characteristic of object evaluated by the image analyzer 231 corresponds to a single energy X-ray image, a first energy X-ray signal is transmitted to the second image processor 233b, and, thus, a single energy X-ray image is generated without further radiation of X-rays.

An exemplary embodiment using a method for acquiring a multiple energy X-ray image by radiating a plurality of X-rays from the X-ray generator is described above. Hereinafter, an exemplary embodiment using a method for separating X-rays according to respective energy bands in the X-ray detector is described below.

Figure 7:
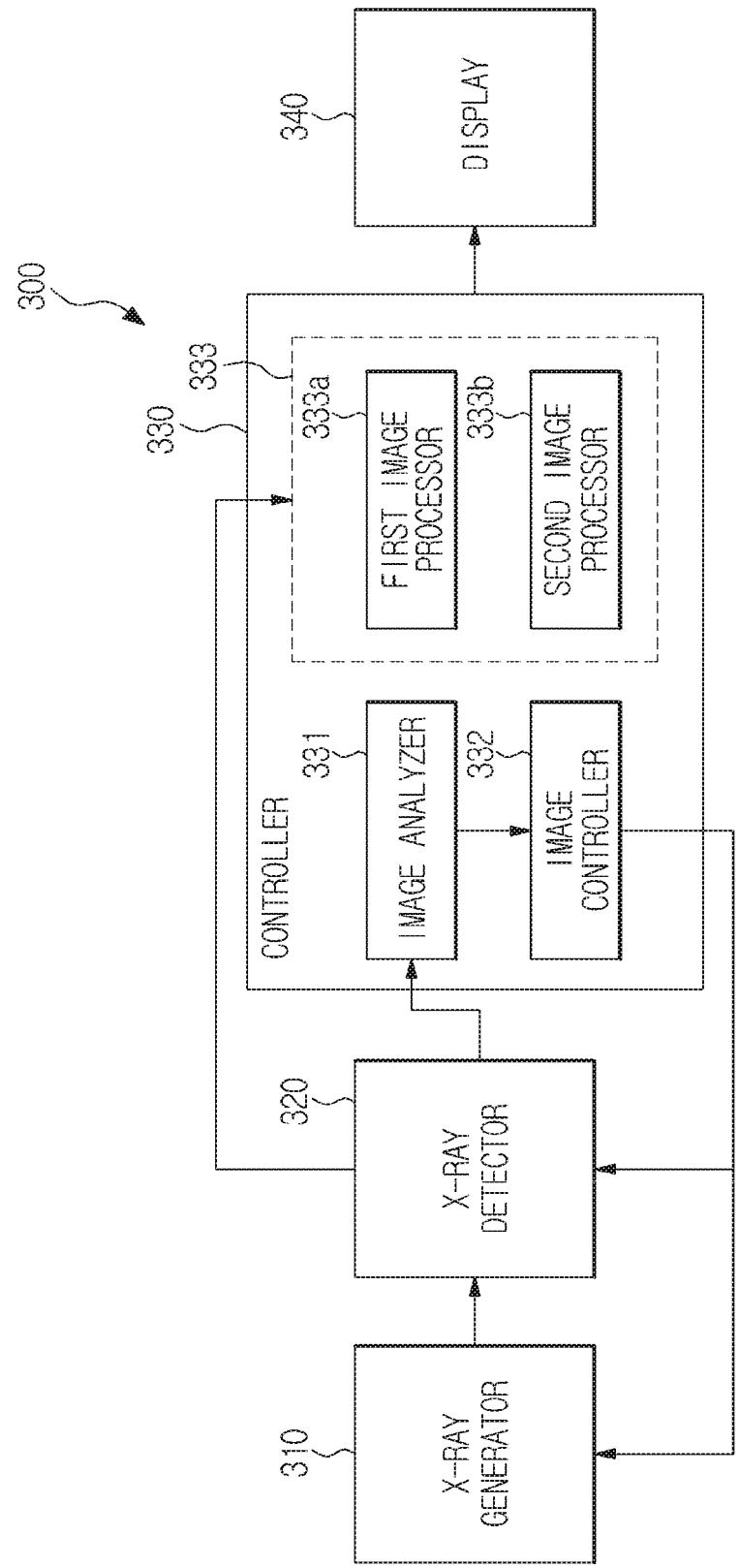
FIG. 7 is a block diagram illustrating a configuration of an X-ray imaging device according to an exemplary embodiment.

FIG. 7 is a block diagram illustrating a configuration of an X-ray imaging device according to an exemplary embodiment.

Referring to FIG. 7, the X-ray imaging device 300 includes an X-ray generator 310 to generate X-rays, an X-ray detector 320 to detect the X-ray passing through the object, a controller 330 to evaluate characteristics of the object using the detected X-rays and produce a single energy X-ray image or a multiple energy X-ray image, based on the evaluated results, and a display 340 to display the X-ray image.

The X-ray generator 310 may perform pre-shot by radiating a reduced dose of X-rays. The X-rays radiated from the X-ray generator 310 may be a wide band X-ray including a wide energy band which is an energy band including a plurality of different single energy bands. The energy band of the radiated X-ray may be changed depending on object type. For example, when imaging the chest X-rays having an energy band of about 10 to about 140 keV may be radiated, and when imaging the breast, X-rays having an energy band of about 10 to about 50 keV may be radiated.

The radiated X-rays pass through the object and are detected by the X-ray detector 320.

Figure 8:
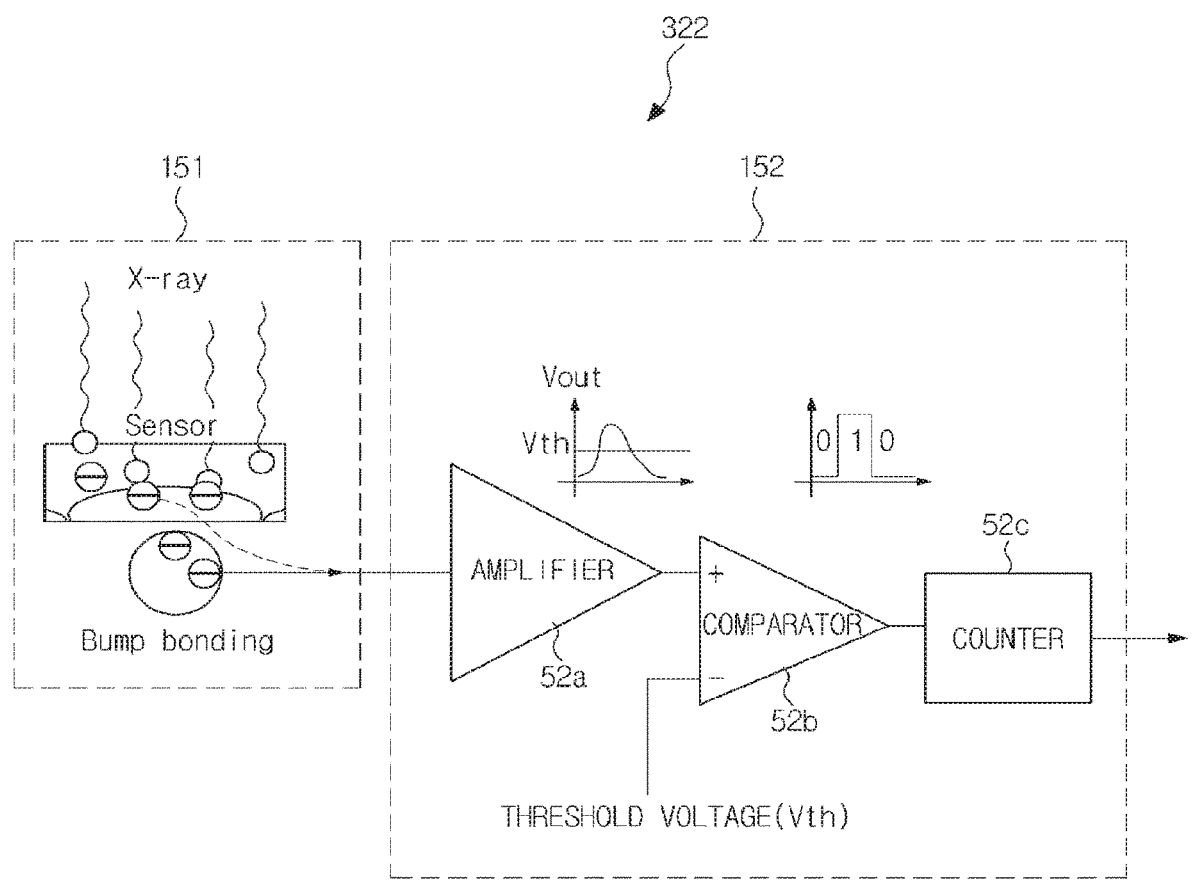
FIG. 8 is a circuit view illustrating a portion of the photon counting detector (PCD)

The X-ray detector 320 includes a photon counting detector (PCD) 322 and separates the detected X-rays according to energy band. In FIG. 8, a circuit view of the pixel area of the PCD is shown.

Referring to FIG. 8, the PCD 322 is divided into a sensor region 151 to detect X-rays and a readout circuit region 152, and the sensor region may include a light-receiving device such as photodiode. The two regions may be connected to each other by bonding such as bump bonding. When the X-rays passing through the object reach the sensor region 151 of the PCD, electrons which stay in a valance band receive a photon energy of the X-ray and are then excited to a conduction band across a band gap indicating an energy difference. A great amount of electron-hole pairs are produced in a depletion region due to excitation, and electrons and holes are moved in opposite directions based on an electric field applied to the sensor region 151.

The electrons or holes moved based on the electric field are input to the readout circuit region 152 through bump bonding, and an amplifier 52a of the readout circuit region 152 charges an input charge generated from one photon and outputs a voltage signal corresponding thereto. When the output voltage signal is input to the comparator 52b and a voltage corresponding to an energy band to be separated is input as a threshold voltage, the comparator 52b compares the input voltage signal with the threshold voltage, outputs the comparison results as pulses and input the same to the counter 52c. The counter 52c counts the number of output pulses of the comparator per unit time and measures X-ray intensity (represented as the number of photons) with a predetermined energy band among incident X-rays.

When X-rays passing through the object are detected according to respective bands separated into a first energy band, second energy band and third energy band, the readout circuit region 52 may include three comparators corresponding to the energy bands.

A signal output from the X-ray detector 320 is an X-ray image signal of each energy band. In the present exemplary embodiment, the X-ray image signal includes information associated with the number of photons present in each pixel. The signals output from the X-ray detector 320 are a first energy image signal, a second energy image signal and a third energy image signal. The image signals may be output from the entire energy band which is not separated.

Since evaluation of object characteristics are carried out during pre-shot and an image output from the display 340 is acquired during main imaging, the X-ray detector 320 may output an image signal in the entire energy band, instead of separating X-rays according to energy bands.

Referring to FIG. 7 again, the controller 330 includes an image analyzer 331 to analyze an image signal and evaluate characteristics of the object, an image controller 332 to control an X-ray generator 310 or X-ray detector 320, based on the analysis results of the image analyzer 331, and an image processor 333 to produce a multiple energy X-ray image or a single energy X-ray image.

The image analyzer 331 analyzes at least one of image signals output from the X-ray detector 320 and evaluates object characteristics. The image signal used for analysis may be the first energy image signal, the second energy image signal, the third energy image signal or any image signal of the entire energy band.

The image analyzer 331 evaluates tissue properties of the object and, in an exemplary embodiment, the image analyzer 331 determines breast density. Operation of the image analyzer 331 is described in detail above and a detailed description thereof is thus omitted.

The image controller 332 determines whether the characteristic of object corresponds to a multiple energy X-ray image or a single energy X-ray image, based on the determination results of the image analyzer 331, controls the X-ray generator 310 or the X-ray detector 320 based on the result and begins main imaging.

When the characteristic of object corresponds to a multiple energy X-ray image, a broadband X-ray having a greater dose than X-rays radiated from the X-ray generator 310 during pre-shot is radiated to the object and the X-ray detector 320 detects X-rays passing through the object. The energy band of radiated X-rays may be the same as the energy band of X-ray radiated during pre-shot and may be newly set, based on characteristics of the object.

The X-ray detector 320 detects the X-ray, converts the same into a voltage signal and separates the converted voltage signal according to predetermined energy bands. The separated energy band may be set by the image controller 332 or the user according to object type, or by the image controller 332 depending on object characteristics analyzed in the image analyzer 331. Image signals of the image are acquired according to individual energy bands and the acquired image signals are transmitted to the first image processor 333a.

The first image processor 333a performs multiple energy image processing on the image signals according to individual energy bands, produces a multiple energy X-ray image with an improved contrast between tissues and displays the image on the display 340. The image processing operation of the first image processor 333a is described in detail above.

In the present exemplary embodiment, characteristics of the object are evaluated by analyzing image signals acquired by pre-shot, but in another exemplary embodiment, characteristics of the object may be evaluated by analyzing image signals acquired by main imaging.

Figure 9:
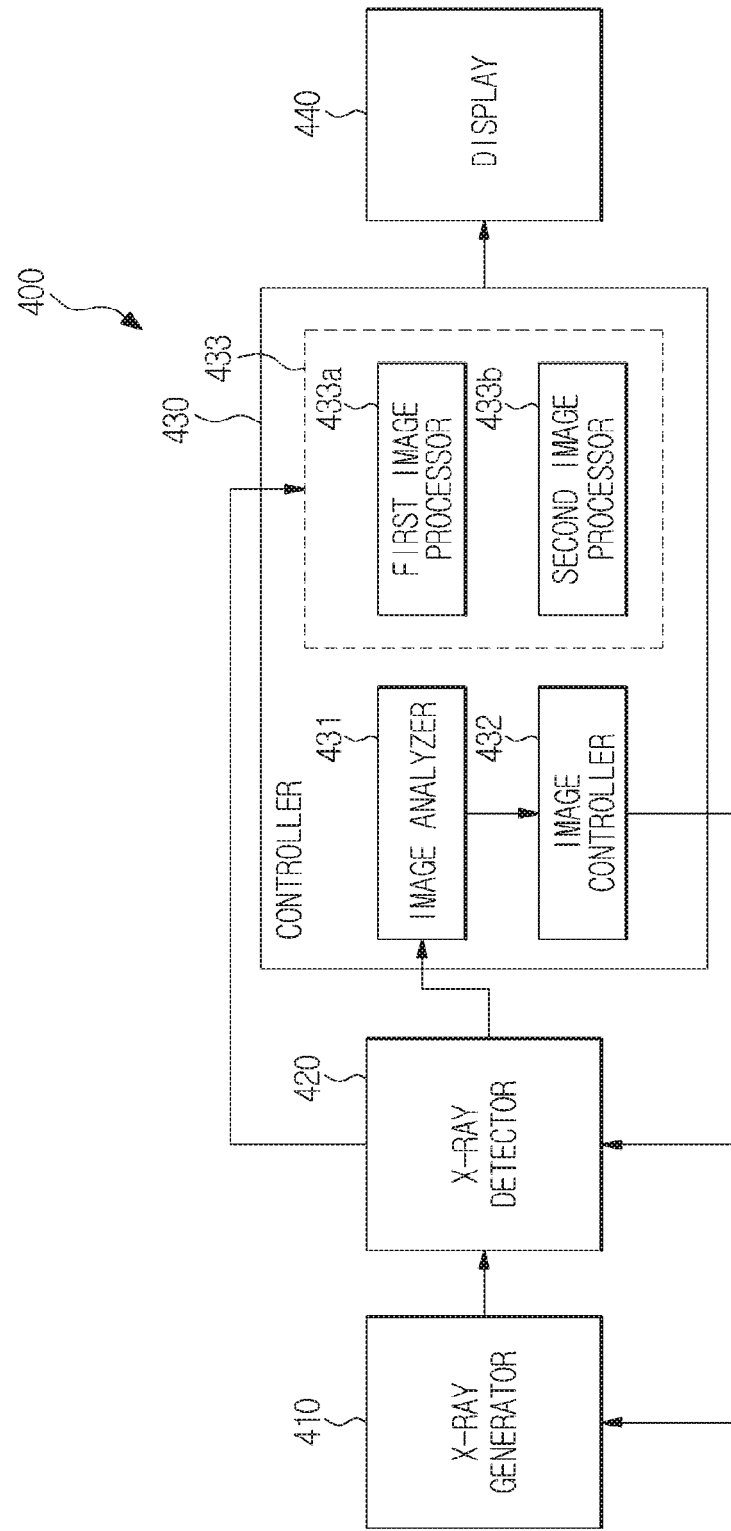
FIG. 9 is a block diagram illustrating an X-ray imaging device according to an exemplary embodiment.

FIG. 9 is a block diagram illustrating an X-ray imaging device according to an exemplary embodiment.

In a case of using a method of detecting X-rays according to individual energy bands to obtain a plurality of X-ray images, X-ray dose may be decreased even during main imaging, an energy band suitable for characteristics of an object may be set once after X-rays are radiated and pre-shot may be thus not performed. The X-ray imaging device 400 according to the exemplary embodiment of FIG. 9 analyzes image signals acquired during main imaging, regardless of performance of pre-shot.

The X-ray generator 410 radiates a broadband X-ray including a plurality of energy bands to an object. X-rays passing through the object are converted into an electric signal by the X-ray detector 420 and the X-ray detector 420 including the PCD separates the converted electric signals into individual energy bands predetermined according to object type, or separates only an energy band used for determination of object characteristics or acquires an image signal of the entire energy band.

The image analyzer 431 of the controller 430 analyzes image signals of the object and evaluates characteristics of the object. The image signal used for evaluation of characteristics of the object is one of image signals converted by the X-ray detector 420. When the X-ray detector 420 separates the X-ray into predetermined individual energy bands, one of the separated energy bands may be selected and analyzed. For example, when imaging the breast, an image signal corresponding to a low energy band may be analyzed, and when imaging the chest, an image signal corresponding to a high energy band may be analyzed. The evaluation of characteristics of the object is described in detail above.

The image controller 432 determines whether the characteristic of object determined in the image analyzer 431 corresponds to a multiple energy X-ray image or a single energy X-ray image.

Generation of a multiple energy X-ray image or a single energy X-ray image according to an exemplary embodiment will be described in detail below.

When the X-ray detector 420 acquires a plurality of image signals according to a plurality of individual energy bands, the image signals are stored in a memory (not shown) provided in the X-ray detector 420 or the controller 430.

When the imaging controller 432 determines that the characteristic of the object corresponds to a multiple energy X-ray image, the memory transmits the image signals to a first image processor 433a, and the first image processor 433a produces a multiple energy X-ray image with improved contrast between tissues through multiple energy image processing.

When the imaging controller 432 determines that the characteristic of object corresponds to a single energy X-ray image, the memory transmits one of the image signals to the second image processor 433b. The image signal transmitted to the second image processor 433b may be determined depending on type or characteristics of the object and may be an image signal used for the image analyzer 431.

In a case in which the X-ray detector 420 separates only an energy band used for evaluation of characteristics of the object, when the characteristic of object corresponds to a multiple energy X-ray image, X-rays are separated at a not-separated band among the energy bands, image signals at respective energy bands and image signals used for evaluation of characteristics of the object are transmitted to the first image processor 433a. When the characteristic of object corresponds to a single energy X-ray image, the image signal used for evaluation of characteristics of the object is transmitted to the second image processor 433b.

In a case in which the X-ray detector 420 converts the entire energy band of X-rays into an image signal, instead of separating the X-ray, when the characteristic of the object corresponds to a multiple energy X-ray, the image X-ray detector acquires image signals of respective energy bands and transmits the same to the first image processor 433a. When the characteristic of the object corresponds to a single energy X-ray image, the image X-ray detector transmits the entire energy band of image signal to the second image processor 433b, or the X-ray detector 420 acquires an image signal of the single energy band determined according to type or characteristic of object and transmits the same to the second image processor 433b.

The energy bands separated by the X-ray detector 420 or the single energy band may be predetermined by the user or the imaging controller 432 depending on type or thickness of object, or by the imaging controller 432 depending on object characteristics evaluated by the image analyzer 431.

In an exemplary embodiment, both a multiple energy X-ray image and a single energy X-ray image may be produced and displayed on a display 440.

Figure 10A:
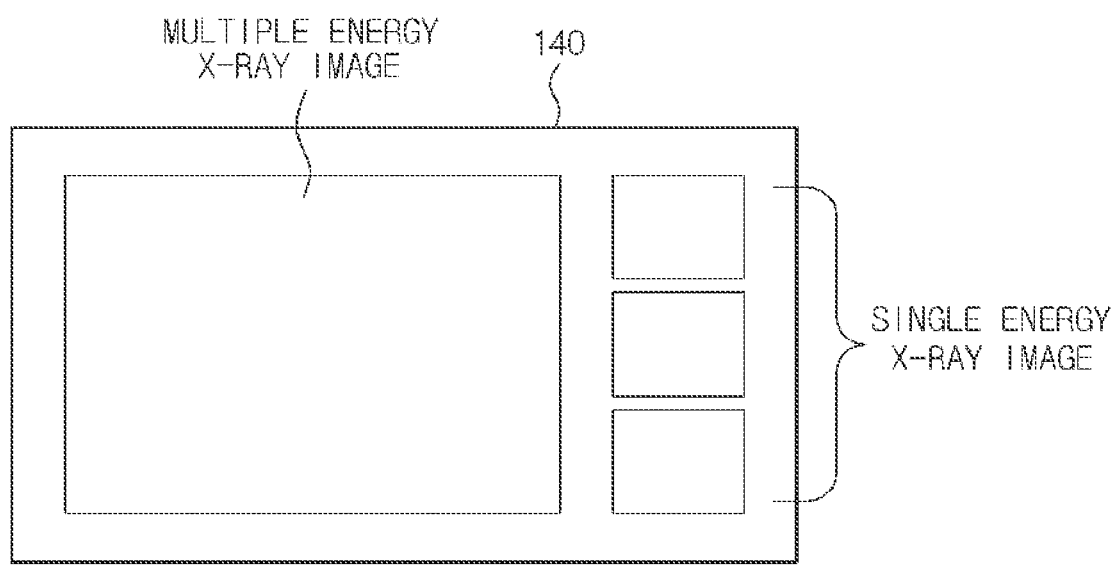
FIGS. 10A and 10B illustrate an example of an image displayed on a display.
Figure 10B:
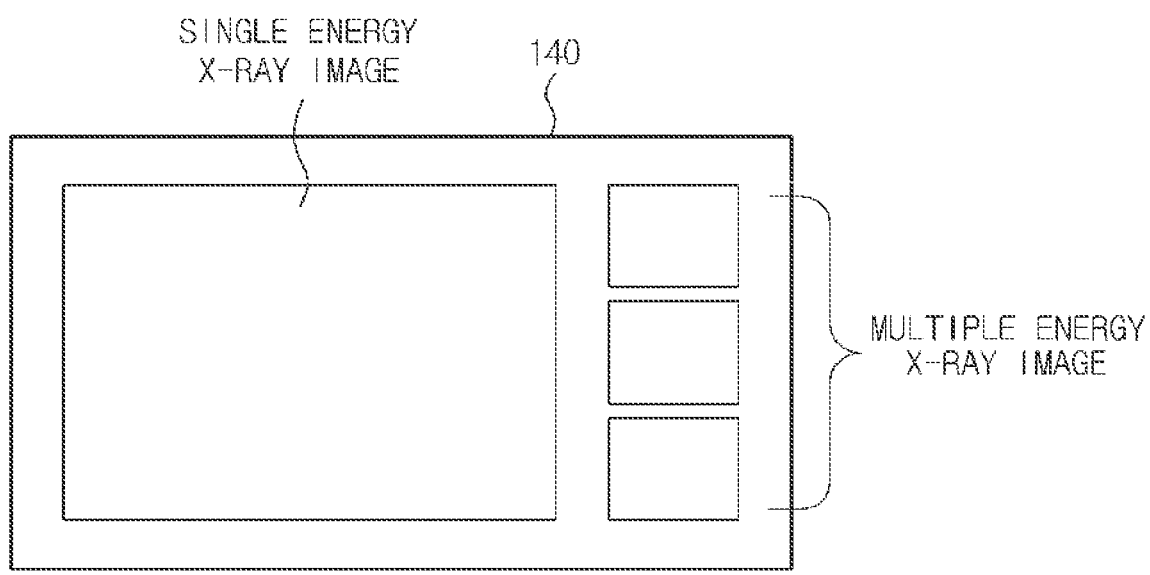

FIGS. 10A and 10B illustrate an example of an image displayed on a display. The display 140 of FIGS. 10A and 10B includes displays 240, 340 and 440 of X-ray imaging devices 200, 300 and 400 according to embodiments.

When, as a result of evaluation of object characteristics, a multiple energy X-ray image is determined to be produced, a single energy X-ray image of the object is produced together with the multiple energy X-ray image thereof, as shown in FIG. 10A, the multiple energy X-ray image is mainly displayed on the display 110 and the single energy X-ray image is subsidiarily displayed thereon.

In addition, when, as a result of evaluation of characteristics of the object, a single energy X-ray image is determined to be produced, a multiple energy X-ray image of the object is produced together with the single energy X-ray image thereof, as shown in FIG. 10B, the single energy X-ray image is mainly displayed on the display 110 and the multiple energy X-ray image is subsidiarily displayed thereon.

The user reads out a multiple energy X-ray image with improved contrast between tissues of an object and a single energy X-ray image with superior image quality and thereby more accurately performs diagnosis.

Hereinafter, a method for producing an X-ray image according to an embodiment will be described in detail.

FIG. 11 is a flowchart illustrating a method for producing an X-ray image according to an exemplary embodiment. In the present exemplary an image signal acquired during pre-shot is analyzed, in a method for radiating X-rays several times in order to acquire a multiple energy X-ray image.

Referring to FIG. 11, for pre-shot, X-rays are radiated to an object (operation 611). The radiated X-ray dose is decreased by decreasing tube current and exposure time, as compared to main imaging and the X-ray energy band may be suitably set according to the object. For example, when imaging the chest, a high energy band of about 120 to about 140 keV may be set and when imaging the breast, a low energy band of about 10 to about 30 keV may be set.

In operation 612, X-rays passing through the object are detected. An image signal is acquired (operation 613). As described above, X-rays passing through the object are detected at each pixel by the X-ray detector and the detected X-rays are converted into an electric signal. The electric signal may be an analog signal or a digital signal. When all the electric signals of respective pixels are combined, one image of the object may be acquired and the electric signal corresponds to an image signal of the object.

The acquired image signal is analyzed and object characteristics are evaluated (operation 614). The object characteristics include characteristics affecting image analysis and are associated with inner structures of the object, as for example, at least one of tissue composition, ratios of respective tissues and a ratio of specific tissue of the object.

For example, when imaging the breast, the breast density is determined. The breast density may be represented by a ratio of a parenchymal tissue with respect to the total breast tissue, and a reference value, providing an estimation basis of the parenchymal tissue, may be predetermined according to experiments, statistics or theory.

In operation 615, it is determined that the determined characteristic of the object corresponds to a multiple energy X-ray image (YES), and the multiple energy X-ray image is produced by performing main imaging.

For this purpose, a plurality of X-rays having different energy bands are radiated to the object (operation 616). This means that X-rays are radiated several times from the X-ray generator and the X-rays of different bands may be sequentially radiated. The energy band of the radiated X-rays and the number of X-ray irradiation may be predetermined depending on object type or may be set depending on object characteristics evaluated by analyzing image signals.

The radiated X-ray pass through the object and a plurality of X-rays passing through the object are detected and are converted into a plurality of image signals (operation 617). The flowchart shows that the X-rays are radiated and then detected. This disclosure is given for convenience of description only. In an exemplary embodiment, a first X-ray is radiated, the following X-ray is radiated, and the X-rays are then detected.

The image signals are subjected to multiple energy image processing to produce a multiple energy X-ray image (operation 618). The multiple energy image processing enables one image with an improved contrast between tissues to be acquired from the image signals, as described in detail above.

The produced multiple energy X-ray image is displayed on the display (operation 619). A user analyzes dense breast using a multiple energy X-ray image with an improved contrast between tissues and thereby efficiently determines presence of lesions.

If, in operation 615, it is determined that the determined characteristic of object does not correspond to a multiple energy X-ray image (NO), the characteristic of the object corresponds to a single energy X-ray image, and a single energy X-ray image is produced by performing main imaging.

For this purpose, X-rays having a single energy band are radiated to an object (operation 621). An energy of the radiated X-rays may be the same as an energy of X-rays radiated during pre-shot, but X-ray dose may be increased by increasing tube current and exposure time, as compared to pre-shot.

The X-ray passing through the object is detected (operation 622) and an image signal is acquired (operation 623). The converted image signal is subjected to image processing to produce a single energy X-ray image (operation 624). The image processing means image processing generally used for generation of the X-ray image and a detailed explanation thereof is thus omitted.

The obtained image is displayed on the display (operation 625).

Figure 12:
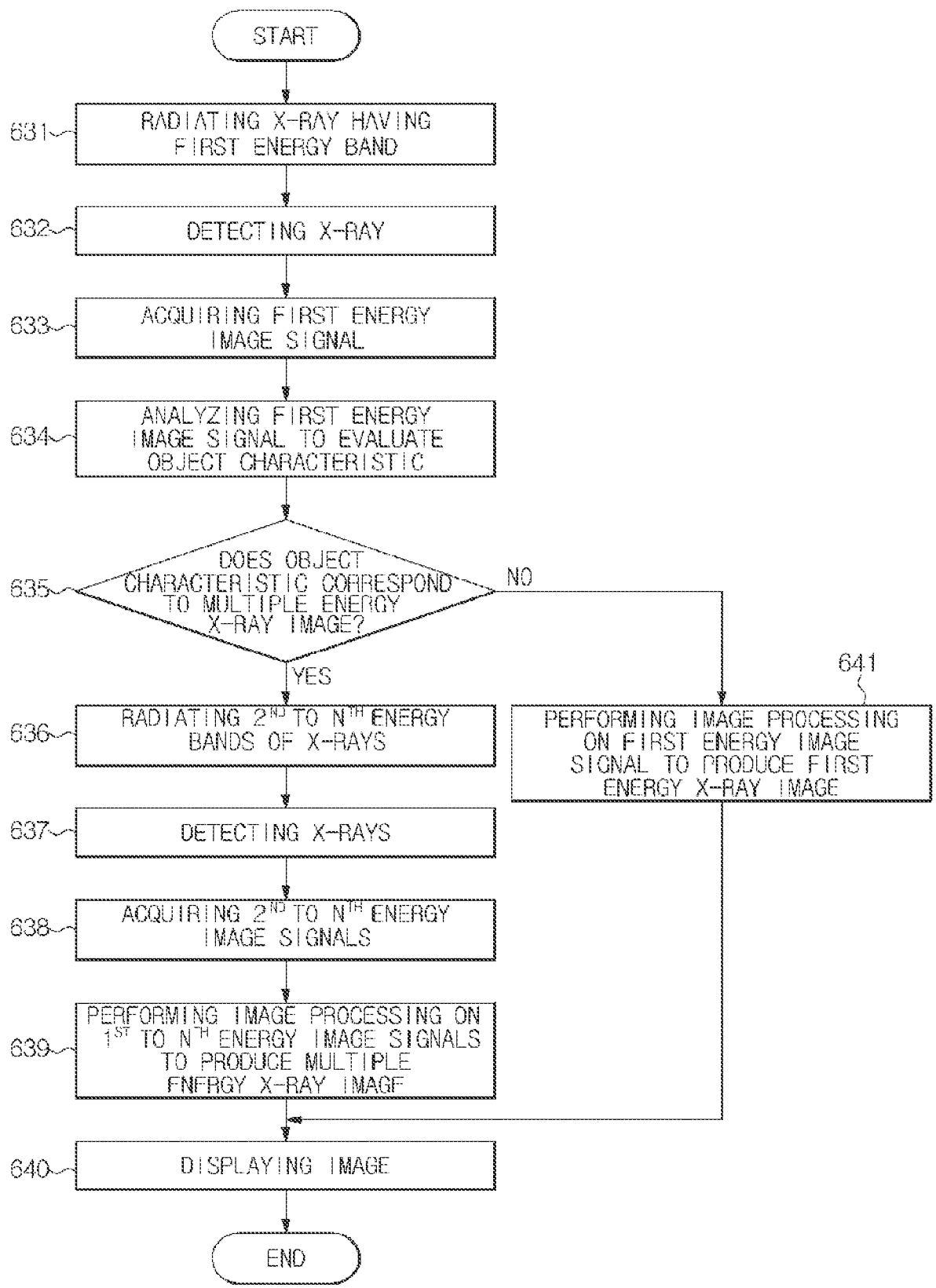
FIG. 12 is a flowchart illustrating a method for producing an X-ray image according to an exemplary embodiment.

FIG. 12 is a flowchart illustrating a method for producing an X-ray image according to an exemplary embodiment. In the present exemplary embodiment the pre-shot is not performed.

Referring to FIG. 12, an X-ray with a first energy band is radiated to the object (operation 631). The first energy band X-ray may be used for generation of the single energy X-ray image and a first level of energy may be changed depending on object type.

The X-ray passing through the object is detected (operation 632), and a first energy image signal of the object is acquired from the detected X-ray (operation 633). The first energy image signal corresponds to an image signal indicating a general single energy X-ray image.

The first energy image signal is analyzed and characteristics of the object are evaluated (operation 634). The evaluation of object characteristics is described with reference to FIG. 8 above and a detailed explanation thereof is thus omitted.

Based on a result of evaluation of characteristics of the object, it is determined that the characteristic of object corresponds to a multiple energy X-ray image (operation 635), as for example, when the tissues of the object are dense and/or an image with an improved contrast between the tissues is needed, and a multiple energy X-ray image of the object is produced.

For this purpose, $2^{nd}$ to $n^{th}$ energy (n≥2, in which n is an integer) bands of X-rays are radiated to the object (operation 636). The $2^{nd}$ to $n^{th}$ energy bands are different energy bands and are different from the first energy band. X-rays of different energy bands are sequentially radiated from the X-ray generator and the $1^{st}$ to $n^{th}$ energy bands may indicate an X-ray irradiation order and may be unrelated to energy levels. The energy level of X-rays and the number (n) of different energy bands may be predetermined depending on object type and may be set depending on object characteristics evaluated by analyzing image signals.

The $2^{nd}$ to $n^{th}$ energies passing through the object are detected (operation 637) and $2^{nd}$ to $n^{th}$ energy image signals of the object are acquired from the detected X-rays (operation 638). The flowchart discloses that $2^{nd}$ to $n^{th}$ energy X-rays are radiated and then detected. This disclosure is given only for convenience of description. In the exemplary embodiment, a second energy X-ray is radiated, the following X-ray is radiated and the X-rays are then detected.

The $1^{st}$ to $n^{th}$ energy image signals are subjected to multiple energy image processing to produce a multiple energy X-ray image (operation 639), and the produced image is displayed on the display (operation 640). The first energy image signal is the image signal used for evaluation of characteristics of the object.

When it is determined, in operation 635, that object characteristics does not correspond to a multiple energy X-ray image (NO), as for example, when the tissues of the object are not dense and/or detection of lesions or other effects is possible with a single energy X-ray image, the single energy X-ray image of the object is produced.

For this purpose, the acquired first energy image signal is subjected to image processing to produce a first energy X-ray image (operation 641), and the image is displayed on the display (operation 640).

Figure 13:
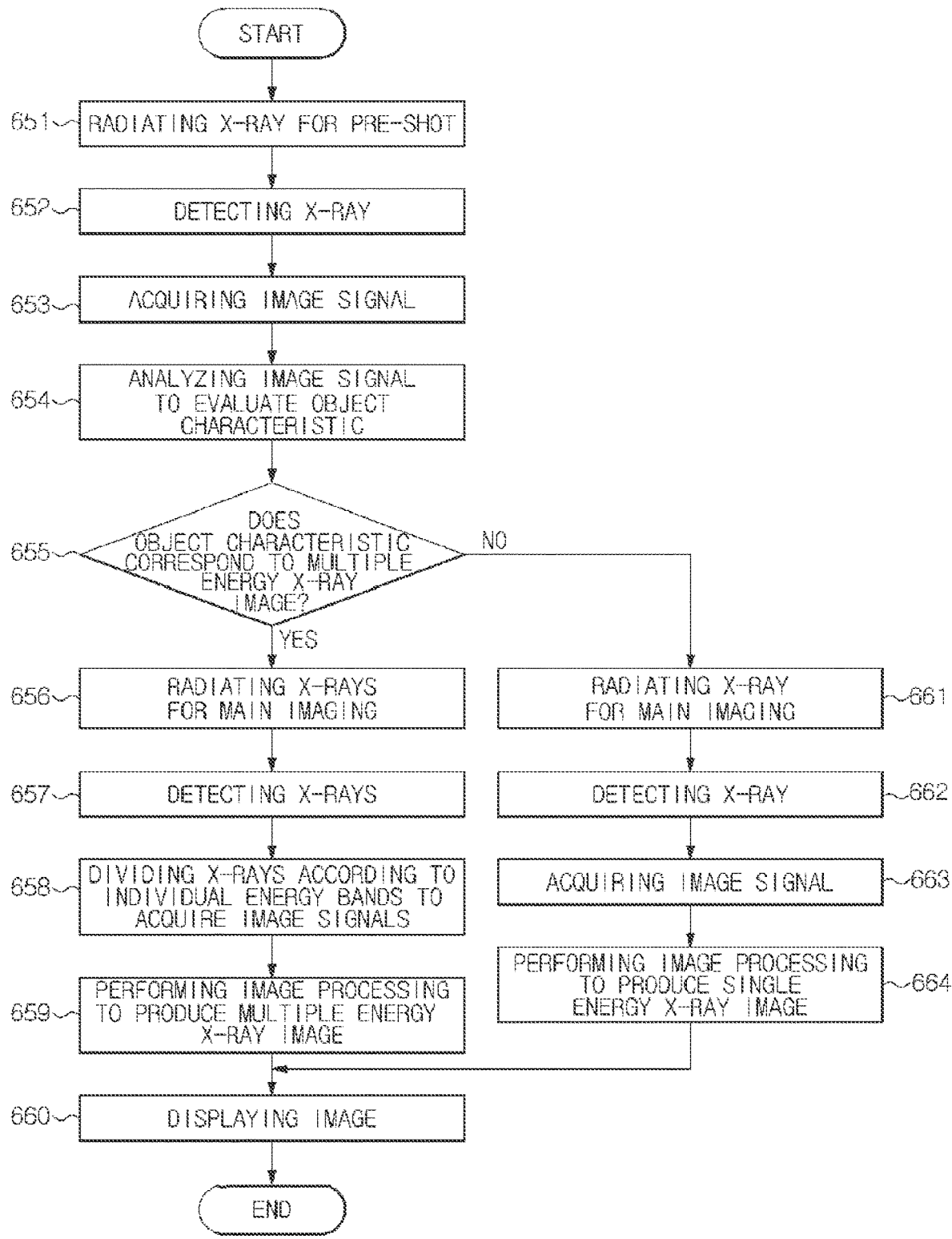
FIG. 13 is a flowchart illustrating a method for producing an X-ray image according to an exemplary embodiment.

FIG. 13 is a flowchart illustrating a method for producing an X-ray image according to an exemplary embodiment. In the present exemplary embodiment, the pre-shot is performed.

Referring to FIG. 13, X-rays are radiated to the object, for pre-shot (operation 651). The radiated X-ray has a dose or irradiation amount which is decreased by decreasing a tube current and an exposure time, and the X-rays may have an energy band set according to object type and may be a broadband X-ray including a plurality of energy bands.

The X-ray passing through the object is detected (operation 652) and an image signal of the object is acquired from the detected X-ray (operation 653). When the radiated X-ray is a polychromatic X-ray having a predetermined energy band, an energy band suitable for the object may be separated during acquisition of an appropriate image signal. For example, when imaging the breast, an image signal of an energy band of about 30 keV or less is acquired.

An image signal of the object is analyzed and characteristics of the object are evaluated (operation 654). The evaluation of characteristics of the object is described in detail above.

In operation 655, it is determined that the determined characteristic of the object corresponds to a multiple energy X-ray image (YES), as for example, when the tissues of the object are dense and/or an image with improved contrast between tissues is needed, and a multiple energy X-ray image of the object is produced.

For this purpose, X-rays are radiated to the object to begin main imaging (operation 656). The radiated X-rays may be polychromatic X-rays having a predetermined energy band and include both a low energy band and a high energy band. For example, when imaging the breast, X-rays with a 10-50 keV band may be radiated.

The X-rays passing through the object are detected (operation 657) and the detected X-rays are divided according to individual energy bands to acquire a plurality of image signals (operation 658). The separation of the energy bands may be predetermined depending on object type or be set in consideration of object characteristics. The image signals are image signals of individual energy bands.

The image signals are subjected to multiple energy image processing to produce a multiple energy X-ray image with improved contrast between tissues (operation 659), and the produced image is displayed on the display (operation 660).

When, in operation 655, it is determined that the characteristic of object does not correspond to a multiple energy X-ray image (NO), as for example, when the tissues of the object are not dense and/or detection of lesions is possible with a single energy X-ray image, a single energy X-ray image of the object is produced.

For this purpose, X-rays are radiated to the object to begin main imaging (operation 661). An X-ray of a specific energy band set according to type or properties of the object may be radiated and a broadband X-ray including the specific energy band may be radiated.

The X-ray passing through the object is detected (operation 662) and an image signal of the object is acquired from the detected X-ray (operation 663). When the radiated X-ray is a broadband X-ray having a specific energy band, an X-ray with a specific energy level set according to type or characteristic of object is separated from the detected broadband X-ray and an image signal corresponding to the corresponding energy level may be acquired.

The acquired image signal is subjected to image processing to produce a single energy X-ray image (operation 664) and the produced image is displayed on the display (operation 660).

Figure 14:
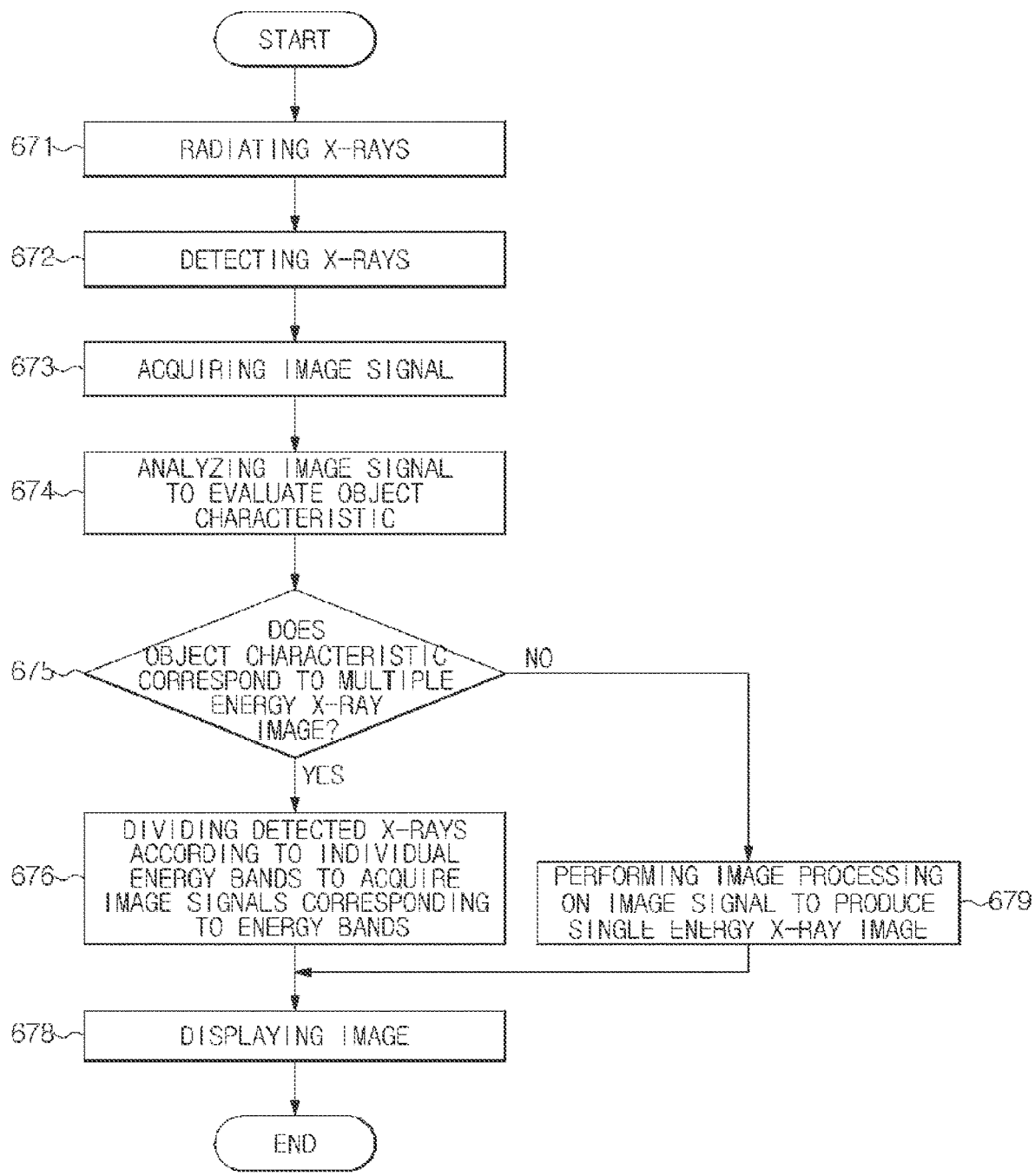
FIG. 14 is a flowchart illustrating a method for producing an X-ray image according to an exemplary embodiment.

FIG. 14 is a flowchart illustrating a method for producing an X-ray image according to an exemplary embodiment. In the present exemplary embodiment, the pre-shot is not performed.

Referring to FIG. 14, an X-ray is radiated to the object (operation 671). The radiated X-ray is an X-ray for main imaging which includes a plurality of energy bands set depending on the object.

The X-ray passing through the object is detected (operation 672) and an image signal of the object is acquired from the detected X-ray (operation 673).

Characteristics of the object are evaluated by analyzing image signals (operation 674). The evaluation of object characteristics is described above.

In operation 675, it is determined that the characteristic of the object corresponds to a multiple energy X-ray image (YES), as for example, when the tissues of the object are dense and/or an image with improved contrast between tissues is needed, and a multiple energy X-ray image of the object is produced.

For this purpose, the X-rays detected in (operation 672) are divided according to individual energy bands and a plurality of image signals corresponding to the energy bands are acquired (operation 676). The divided energy bands may be set depending on type or characteristics of the object.

The acquired image signals are subjected to multiple energy image processing to produce a multiple energy X-ray image (operation 677) and the produced image is displayed on the display (operation 678).

When in operation 675, it is determined that the characteristic of object corresponds to a single energy X-ray image (NO), as for example, when the tissues of the object are not dense and/or detection of lesions is possible with a single energy X-ray image, a single energy X-ray image of the object is produced (operation 679).

For this purpose, the acquired image signal acquired is subjected to image processing to produce a single energy X-ray image (operation 679). That is, an X-ray image corresponding to the entire energy band of the detected X-ray may be produced. As another example, an X-ray with a desired energy band is extracted, an image signal is acquired from the extracted X-ray and production of a single energy X-ray image from the image signal is possible. For example, when imaging the breast, an X-ray with a low energy band (10-30 keV) may be extracted and when imaging the chest, an X-ray with a high energy band (120-140 keV) may be extracted.

The produced image is displayed on the display (operation 678) and the user analyzes a single energy X-ray image with superior image quality and thereby detects lesions.

Figure 15:
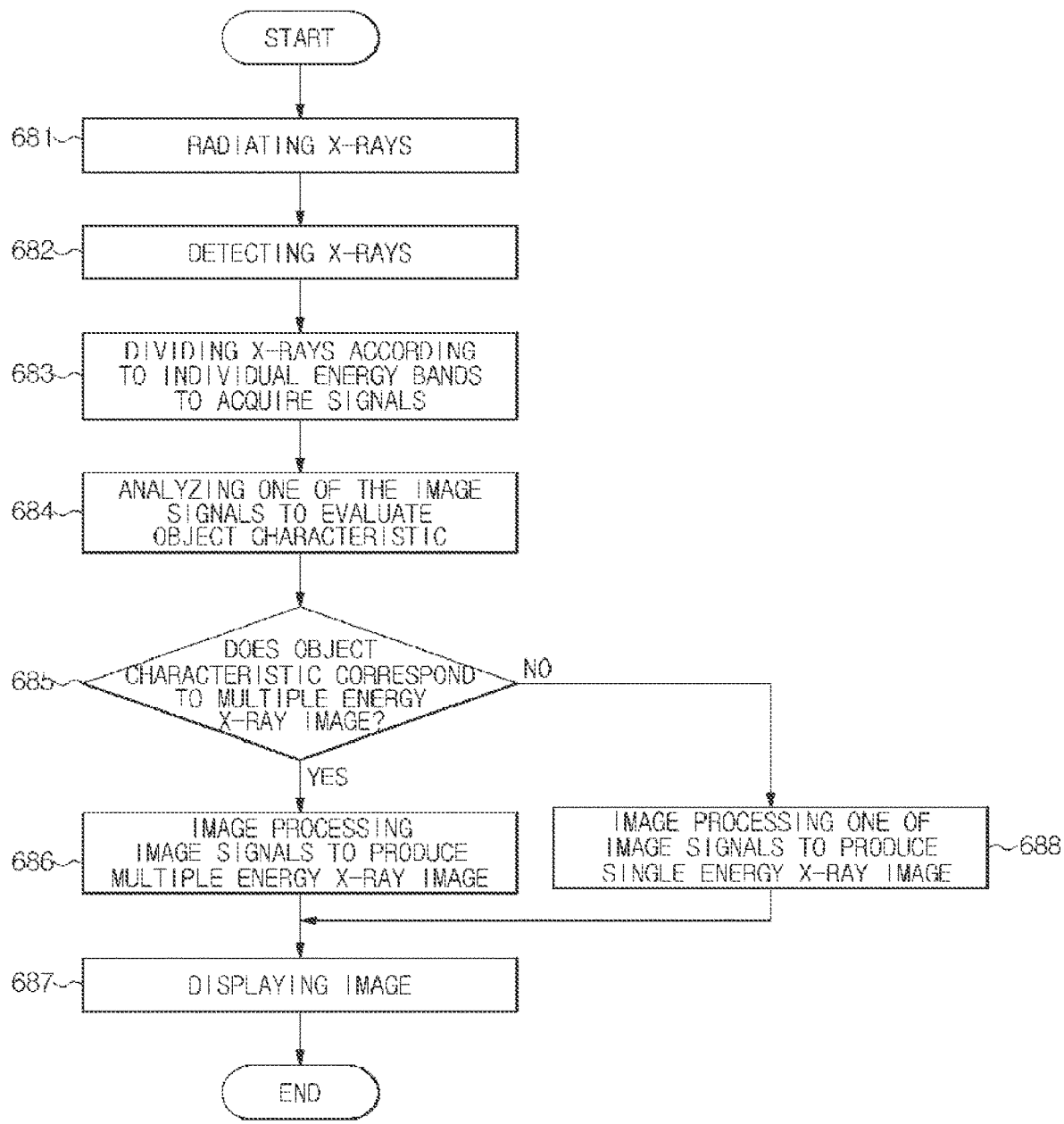
FIG. 15 is a flowchart illustrating a method for producing an X-ray image according to an exemplary embodiment.

FIG. 15 is a flowchart illustrating a method for producing an X-ray image according to an exemplary embodiment. In the present exemplary embodiment the pre-shot is not performed and X-rays are separated into individual energy bands before evaluation of object characteristics.

Referring to FIG. 15, X-rays are radiated to an object (operation 681). The radiated X-rays are used for main imaging and include a plurality of energy bands predetermined depending on the object.

The X-rays passing through the object are detected (operation 682) and the detected X-rays are divided according to individual energy bands to acquire a plurality of image signals (operation 683). An image signal of the entire energy band may be acquired.

One of the image signals is analyzed and characteristics of the object are evaluated (operation 684). The analyzed image signal may be an image signal of the entire energy band, an image signal of a low energy band or an image signal of a high energy band according to the object.

In operation 685, it is determined that the characteristic of the object corresponds to a multiple energy X-ray image (YES), as for example, the tissues of the object are dense and/or an image with improved contrast between tissues is needed, and a multiple energy X-ray image of the object is produced.

For this purpose, the acquired image signals are subjected to multiple energy image processing to produce a multiple energy X-ray image (operation 686) and the produced image is displayed on the display (operation 687).

If, in operation 685, it is determined that the characteristic of object does not correspond to a multiple energy X-ray image (NO), as for example, the tissues of the object are not dense and/or easy detection of lesions is possible with a single energy X-ray image, a single energy X-ray image of the object is produced.

For this purpose, one of the acquired image signals is subjected to image processing to produce a single energy X-ray image (operation 688) and the produced image is displayed on the display (operation 687).

As apparent from the foregoing, at least one of a single energy X-ray image and a multiple energy X-ray image is produced according to tissue characteristics of the object and efficient image analysis is thus possible.

The foregoing exemplary embodiments and advantages are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An X-ray imaging apparatus comprising:
an X-ray generator configured to generate X-rays and radiate the X-rays to an object,
an X-ray detector configured to detect the X-rays that have passed through the object, and obtain a plurality of image signals corresponding to a plurality of energy bands, from the detected X-rays, and
a controller configured to generate a single energy X-ray image and a plurality of multiple energy X-ray images including a first X-ray image generated using an X-ray having a determined energy band that is extracted from the X-rays detected by the X-ray detector,
wherein the plurality of multiple energy X-ray images further include a second X-ray image in which a specific substance is separated, the second X-ray image is generated using the plurality of image signals corresponding to the plurality of energy bands, respectively,
wherein the controller is further configured to control a display to display the single energy X-ray image, the first X-ray image and the second X-ray image together on a same screen of the display.

2. The X-ray imaging apparatus according to claim 1, wherein the specific substance includes at least one from among soft tissues, lesions, and hard tissues, of the object.

3. The X-ray imaging apparatus according claim 1, wherein the object contains a plurality of substances including at least one from among soft tissues, lesions, and hard tissues, and
the specific substance is one of the plurality of substances.

4. The X-ray imaging apparatus according to claim 1, wherein the controller is further configured to control the display to display the single energy X-ray image larger than at least one image from among the first X-ray image and the second X-ray image.

5. The X-ray imaging apparatus according to claim 1, wherein the controller is further configured to display at least one from among the first X-ray image and the second X-ray image larger than the single energy X-ray image.

6. The X-ray imaging apparatus according to claim 1, wherein the plurality of multiple energy X-ray images further include an X-ray image having a region in which a ratio difference between substances is out of a normal range, the region being diacritically marked as an abnormal tissue.

7. The X-ray imaging apparatus according to claim 1, wherein the controller is further configured to obtain image signals with non-imaged energy bands from the plurality of image signals corresponding to the plurality of energy bands.

8. The X-ray imaging apparatus according to claim 1, wherein the controller is further configured to generate the single energy X-ray image corresponding to an entire energy band of the detected X-rays using an image signal corresponding to the entire energy band, and wherein the entire energy band comprises the plurality of energy bands.

9. The X-ray imaging apparatus according to claim 1, wherein the controller is further configured to generate the single energy X-ray image using an image signal corresponding to one of the plurality of energy bands, among the plurality of image signals.

10. The X-ray imaging apparatus according to claim 1, wherein the controller is further configured to control the display to display the single energy X-ray image, the first X-ray image, and the second X-ray image adjacent to each other.

11. The X-ray imaging apparatus according to claim 1, wherein the plurality of multiple energy X-ray images comprises an image generated by using the plurality of image signals, in which a substance of the object has an increased contrast.

12. The X-ray imaging apparatus according to claim 1, wherein the single energy X-ray image comprises an X-ray image corresponding to an entire energy band of the detected X-rays, the X-ray image being generated using an image signal corresponding to the entire energy band, and wherein the entire energy band comprises the plurality of energy bands.

13. The X-ray imaging apparatus according to claim 1, wherein the single energy X-ray image comprises an X-ray image generated using an image signal corresponding to one of the plurality of energy bands, among the plurality of image signals.

14. The X-ray imaging apparatus according to claim 1, wherein, based on the detecting the X-rays by the X-ray detector, the controller is further configured to perform an analysis based on the plurality of image signals and determine a characteristic of the object based on a result of the analysis.

15. The X-ray imaging apparatus according to claim 14, wherein the controller is further configured to determine whether the characteristic of the object corresponds to the single energy X-ray image or at least one of the plurality of multiple energy X-ray images.

16. The X-ray imaging apparatus according to claim 15, wherein the controller is further configured to control the display to display an X-ray image corresponding to the characteristic of the object, among the single energy X-ray image and at least one from among the first X-ray image and the second X-ray image, to be larger than other images among the single energy X-ray image and the at least one from among the first X-ray image and the second X-ray image.

17. The X-ray imaging apparatus according to claim 15, wherein the controller is further configured to determine the characteristic comprising at least one from among a structure of internal tissues, a ratio between at least two of the internal tissues, and a density of a specific internal tissue among the internal tissues, and the internal tissues comprise at least one from among a first substance, a second substance, a third substance, and a fourth substance.

18. The X-ray imaging apparatus according to claim 15, wherein the X-ray generator is further configured to set at least one energy band, among the plurality of energy bands, according to a type of the object or the characteristic of the object.

19. The X-ray imaging apparatus according to claim 15, wherein the X-ray generator is further configured to radiate the X-rays for pre-shot, and the controller is further configured to determine the characteristic of the object based on an image signal obtained from the X-rays radiated for the pre-shot.

20. The X-ray imaging apparatus according to claim 15, wherein the controller is further configured to determine the characteristic of the object based on an image signal used to generate the single energy X-ray image, among the plurality of image signals.

21. The X-ray imaging apparatus according to claim 14, wherein the controller is further configured to calculate a ratio of a parenchymal tissue region to a total breast tissue region, calculate a breast density based on the ratio, and determine whether the breast density exceeds a reference value, and the parenchymal tissue region is included in at least one from among a first substance, a second substance, a third substance, and a fourth substance.

22. The X-ray imaging apparatus according to claim 14, wherein the controller is further configured to set a first energy band for radiating the X-rays, among the plurality of energy bands, based on the characteristic of the object.

23. The X-ray imaging apparatus according to claim 22, wherein, the controller is further configured to set the first energy band lower for imaging the object having a lower attenuation coefficient, and to set the first energy band higher for the imaging the object having a higher attenuation coefficient.

24. The X-ray imaging apparatus according to claim 23, wherein the controller is further configured to set the first energy band lower for the imaging of a breast, and to set the first energy band higher for the imaging of a chest.

25. The X-ray imaging apparatus according to claim 22, wherein the controller is further configured to generate the single energy X-ray image using image signals corresponding to the first energy band, among the plurality of image signals.

26. The X-ray imaging apparatus according to claim 25, wherein the controller is further configured to set second energy bands for radiating the X-rays, among the plurality of energy bands, based on the characteristic of the object, and to generate the plurality of multiple energy X-ray images using image signals corresponding to the second energy bands, respectively, among the plurality of image signals.

27. The X-ray imaging apparatus according to claim 1, the plurality of multiple energy X-ray images further include a third X-ray image in which a plurality of substances are respectively marked.

28. The X-ray imaging apparatus according to claim 27, the controller is further configured to control the display to display the third X-ray image.

29. An X-ray imaging apparatus comprising:
   an X-ray generator configured to generate X-rays and radiate the X-rays to an object,
   an X-ray detector configured to detect the X-rays that have passed through the object, and obtain a plurality of image signals corresponding to a plurality of energy bands from the detected X-rays; and
   a controller configured to generate a single energy X-ray image and a plurality of multiple energy X-ray images including a first X-ray image generated using an X-ray having a determined energy band that is extracted from the X-rays detected by the X-ray detector, wherein the plurality of multiple energy X-ray images further include a second X-ray image in which a specific substance is separated, the second X-ray image is generated using the plurality of image signals corresponding to the plurality of energy bands, respectively, wherein the controller is further configured to control a display to display the single energy X-ray image, the first X-ray image, and the second X-ray image together on a same screen of the display.

30. An X-ray imaging apparatus comprising:

an X-ray generator configured to generate X-rays and radiate the X-rays to an object;

an X-ray detector configured to detect the X-rays that have passed through the object, and obtain a plurality of image signals corresponding to a plurality of energy bands from the detected X-rays; and a controller configured to generate a single energy X-ray image and a plurality of multiple energy X-ray images including a first X-ray image having an increased contrast between a first substance and a second substance and a second X-ray image in which a third substance and a fourth substance are diacritically marked, using the plurality of image signals corresponding to the plurality of energy bands, and control a display to display the first X-ray image and the second X-ray image adjacent to the single energy X-ray image.

31. The X-ray imaging apparatus according to claim 30, wherein the controller is further configured to control the display to display the single energy X-ray image larger than the first X-ray image and the second X-ray image or to display at least one from among the first X-ray image and the second X-ray image larger than the single energy X-ray image.

* * * * *